(12) United States Patent
Lakios et al.

(10) Patent No.: US 10,687,598 B2
(45) Date of Patent: Jun. 23, 2020

(54) ULTRAVIOLET RAZOR BLADE TREATMENT

(71) Applicant: Sensor Electronic Technology, Inc., Columbia, SC (US)

(72) Inventors: Emmanuel Lakios, Mount Sinai, NY (US); Michael Shur, Latham, NY (US); Alexander Dobrinsky, Loudonville, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 413 days.

(21) Appl. No.: 15/444,758

(22) Filed: Feb. 28, 2017

(65) Prior Publication Data

US 2017/0245616 A1 Aug. 31, 2017

Related U.S. Application Data

(60) Provisional application No. 62/301,004, filed on Feb. 29, 2016.

(51) Int. Cl.
| | | |
|---|---|---|
| A45D 27/46 | (2006.01) |
| B26B 21/40 | (2006.01) |
| B08B 3/14 | (2006.01) |
| A61L 2/10 | (2006.01) |
| B08B 3/08 | (2006.01) |
| B08B 5/02 | (2006.01) |
| B08B 3/02 | (2006.01) |
| B08B 7/00 | (2006.01) |
| B26B 21/22 | (2006.01) |
| B08B 3/12 | (2006.01) |
| A61L 2/08 | (2006.01) |

(52) U.S. Cl.
CPC .............. *A45D 27/46* (2013.01); *A61L 2/088* (2013.01); *A61L 2/10* (2013.01); *B26B 21/225* (2013.01); *B26B 21/4037* (2013.01); *A61L 2202/14* (2013.01); *A61L 2202/17* (2013.01)

(58) Field of Classification Search
CPC .. A45D 27/46; B26B 21/225; B26B 21/4037; A61L 2/088; A61L 2/10; A61L 2202/14; A61L 2202/17
See application file for complete search history.

(56) References Cited

U.S. PATENT DOCUMENTS

| | | | |
|---|---|---|---|
| 4,890,348 A | 1/1990 | Racioppi | |
| 5,487,877 A * | 1/1996 | Choi | A47K 5/00 |
| | | | 222/192 |
| 7,553,456 B2 | 6/2009 | Gaska et al. | |
| 7,634,996 B2 | 12/2009 | Gaska et al. | |
| 7,838,846 B2 | 11/2010 | Pinsky | |
| 8,277,734 B2 | 10/2012 | Koudymov et al. | |
| 8,683,701 B1 * | 4/2014 | Loftin | B26B 21/40 |
| | | | 250/455.11 |
| 8,980,178 B2 | 3/2015 | Gaska et al. | |
| 9,006,680 B2 | 4/2015 | Bettles et al. | |

(Continued)

*Primary Examiner* — Benjamin L Osterhout
(74) *Attorney, Agent, or Firm* — LaBatt, LLC

(57) ABSTRACT

An ultraviolet razor blade treatment system for providing a cleaning treatment to a shaving razor is disclosed. The ultraviolet razor blade treatment system can include a shaving razor cleaning unit that has at least one ultraviolet radiation source and sensor to clean surfaces of the shaving razor for purposes of disinfection, sterilization, and/or sanitization.

20 Claims, 10 Drawing Sheets

(56) References Cited

U.S. PATENT DOCUMENTS

| | | |
|---|---|---|
| 9,061,082 B2 | 6/2015 | Gaska et al. |
| 9,138,499 B2 | 9/2015 | Bettles et al. |
| 9,179,703 B2 | 11/2015 | Shur et al. |
| 9,572,903 B2 | 2/2017 | Dobrinsky et al. |
| 9,603,960 B2 | 3/2017 | Dobrinsky et al. |
| 9,687,577 B2 | 6/2017 | Dobrinsky et al. |
| 9,718,706 B2 | 8/2017 | Smetona et al. |
| 10,099,944 B2 | 10/2018 | Smetona et al. |
| 2002/0122743 A1* | 9/2002 | Huang ............... A61L 2/10 422/24 |
| 2003/0034459 A1* | 2/2003 | Bonin ............... A61L 2/06 250/491.1 |
| 2003/0042828 A1* | 3/2003 | Bonin ............... A47B 67/02 312/245 |
| 2003/0101525 A1* | 6/2003 | Belloli ............... A45C 15/06 15/21.1 |
| 2007/0031281 A1* | 2/2007 | Stevens ............... A23L 3/28 422/24 |
| 2008/0168677 A1* | 7/2008 | Miller ............... F26B 9/003 34/202 |
| 2011/0099831 A1* | 5/2011 | Parisi ............... A45D 27/48 34/92 |
| 2013/0048545 A1 | 2/2013 | Shatalov et al. |
| 2014/0060094 A1 | 3/2014 | Shur et al. |
| 2014/0060095 A1 | 3/2014 | Shur et al. |
| 2014/0060096 A1 | 3/2014 | Shur et al. |
| 2014/0060104 A1 | 3/2014 | Shur et al. |
| 2014/0202962 A1 | 7/2014 | Bilenko et al. |
| 2015/0008167 A1 | 1/2015 | Shturm et al. |
| 2015/0069270 A1 | 3/2015 | Shur et al. |
| 2015/0165079 A1 | 6/2015 | Shur et al. |
| 2015/0217011 A1 | 8/2015 | Bettles et al. |
| 2015/0297767 A1 | 10/2015 | Gaska et al. |
| 2015/0336810 A1 | 11/2015 | Smetona et al. |
| 2016/0000953 A1 | 1/2016 | Bettles et al. |
| 2016/0058020 A1 | 3/2016 | Shur et al. |
| 2016/0114186 A1 | 4/2016 | Dobrinsky et al. |
| 2016/0128526 A1 | 5/2016 | Dobrinsky et al. |
| 2016/0375597 A1* | 12/2016 | Broemse ............... H05B 3/0014 30/34.05 |
| 2017/0100495 A1 | 4/2017 | Shur et al. |
| 2017/0100496 A1 | 4/2017 | Shur et al. |
| 2017/0157276 A1 | 6/2017 | Dobrinsky et al. |

* cited by examiner

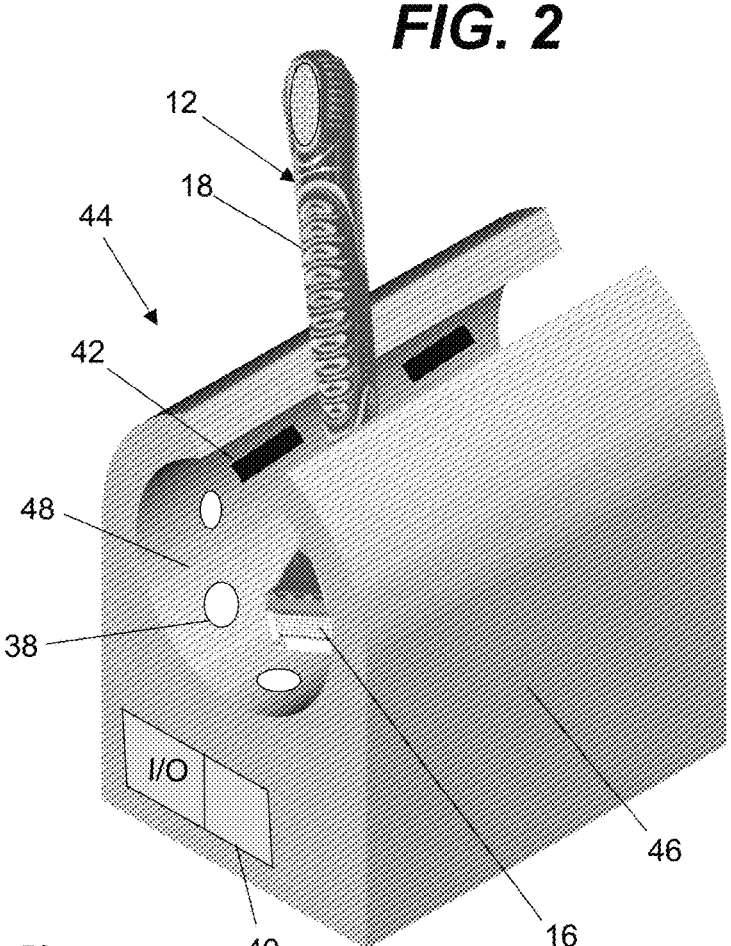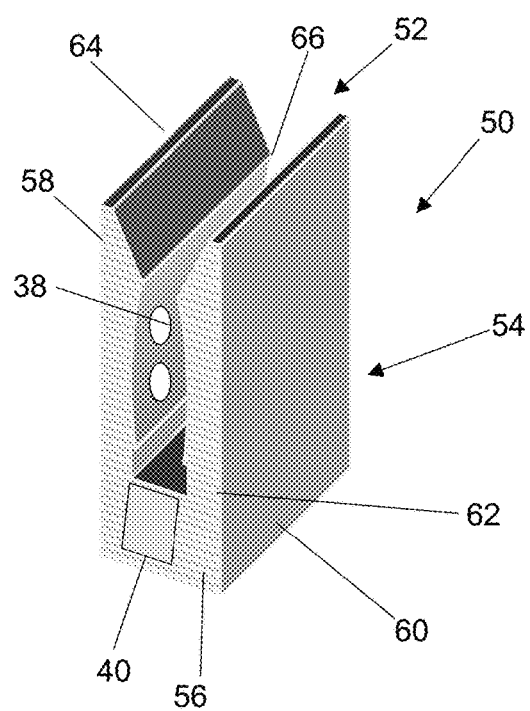

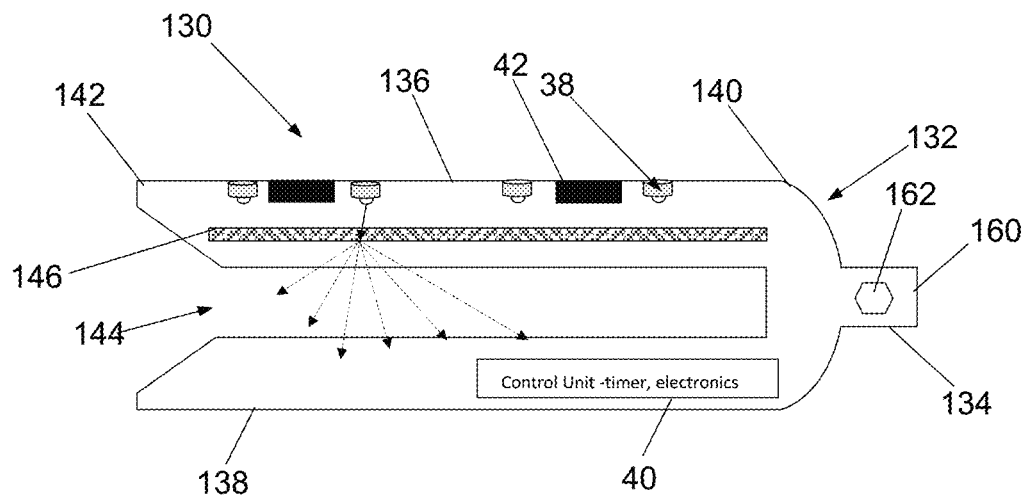
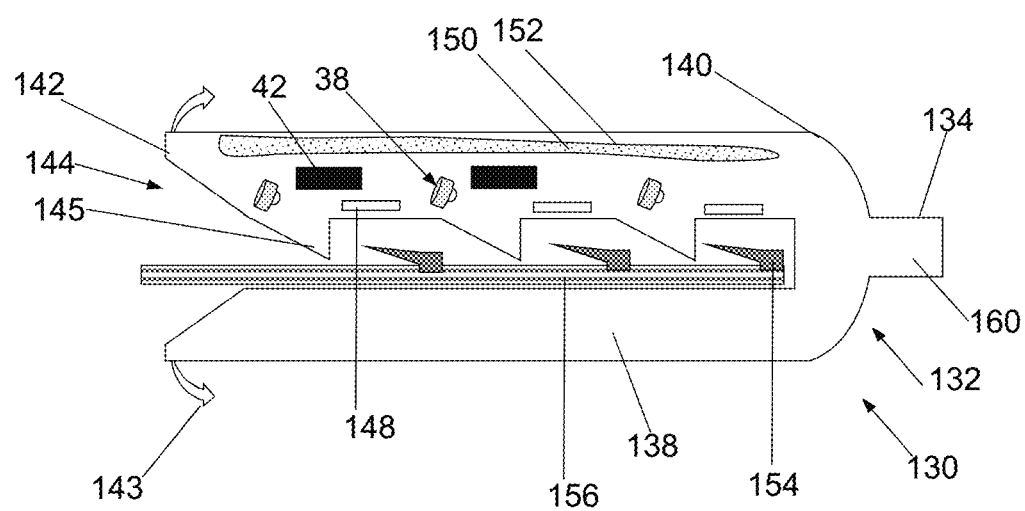

ULTRAVIOLET RAZOR BLADE TREATMENT

REFERENCE TO RELATED APPLICATIONS

The present patent application claims the benefit of U.S. Provisional Application No. 62/301,004, which was filed on 29 Feb. 2016, and which is hereby incorporated by reference.

TECHNICAL FIELD

The disclosure relates generally to shaving, and more specifically, to a solution for using ultraviolet radiation for treating (e.g., disinfecting, sterilizing, sanitizing, and/or the like) shaving razors.

BACKGROUND ART

Shaving to remove hair whether through wet shaving or dry shaving generally involves using a shaving razor or another kind of bladed implement to slice the hair down to skin level or to trim it otherwise close to the skin. The blades that form a shaving razor often become clogged with hair and lubricating fluid that is often used to ease the shaving process. Wet shaving techniques that use a manual razor (e.g., straight razor, safety razor, and multi-bladed razor) typically entail placing the razor through a source of water after each pass of the razor to remove hair and lubricant, while dry shaving techniques that use an electric razor typically can be cleaned after shaving with a brush and/or water. Despite best efforts to keep these razors clean and free of hair and lubricant, there are small spaces that are difficult to clean, especially with multi-bladed razors, and thus, become attractive repositories for shaving debris. This shaving debris can impair the effectiveness of the razor to facilitate a satisfactory shave, which often leads to a user replacing the razor perhaps prematurely, especially with those razors used for wet shaving. Furthermore, the accumulation of shaving debris on the razor can lead to the buildup of germs and bacteria that have the potential to cause adverse health effects.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to ultraviolet cleaning or treating (e.g., disinfecting, sterilizing, sanitizing) of shaving razors to remove bacteria, viruses, germs, and the like. These aspects utilize a shaving razor cleaning unit or system having a housing and at least one ultraviolet radiation source to direct ultraviolet radiation to a razor blade assembly having at least one bladed member for treatment thereof. The shaving razor cleaning unit can operate with wet shaving razors and dry shaving razors. In other aspects, the shaving razor cleaning unit can be integrated with a wet shaving razor or a dry shaving razor to provide a cleaning to its bladed members after use thereof. Thorough cleaning of shaving razors with the shaving razor cleaning units described herein can lead to reduced infections, and life prolongation of the razors.

In one embodiment, the housing can include a base member, a pair of opposing grasping members extending outward from a first side of the base member, and a clamping handle attached to a second side of the base member. Each grasping member can have a first end fixedly attached to the first side of the base member and a second end unattached to the base member. The first end of each grasping member can pivotally attach to opposite ends of the first side of the base member, while the second end of each grasping member can converge towards one another. The clamping handle can have a first clamping handle portion and a second clamping portion that both actuate movement of the second ends of the grasping member from a converging position to a diverging open position configured to receive a razor blade assembly having at least one bladed member. The second ends of the grasping member can grip and cover the razor blade assembly therein in response to the actuating movement being removed from the first clamping handle portion and the second clamping portion. The grasping members can have ultraviolet radiation sources configured to emit ultraviolet radiation towards the front portion and the rear portion of the bladed member of the razor blade assembly in response to the gripping and covering of the assembly.

In one embodiment, the housing can include an open-ended container having a cavity formed therein that is configured to receive the razor blade assembly and substantially surround the razor blade member upon placement therein. In one embodiment, the open-ended container can include a bifurcated cap having a main body portion, a first bifurcated element and a second bifurcated element opposing the first bifurcated element and separated therefrom. The first bifurcated element and the second bifurcated element can each have a first end rigidly fixed to the main body portion and a second end that is flexibly unattached. In this manner, the main body portion, the first bifurcated element and the second bifurcated element form an opening that is configured to receive the razor blade assembly. One or both of the bifurcated elements can include at least one ultraviolet radiation source configured to direct ultraviolet radiation to the bladed member of the razor blade assembly.

In one embodiment, the housing can include a container having one end with a membrane having a flexible opening insertable into a cavity formed in the container that is configured to receive the razor blade assembly and substantially surround the bladed member upon placement therein.

In one embodiment, the housing can include a container having a cavity formed therein, a removable platform suspended in the container that is configured to support the razor blade assembly upon placement therein, and a removable cover that fastens to the container and provides access to the cavity and the platform upon removal thereof. This configuration enables the placement of at least one ultraviolet radiation source on the cover, the sidewalls of the cavity, and/or the bottom surface of the cavity for directing ultraviolet radiation towards the razor blade assembly placed therein.

In one embodiment, the housing can include an open-ended container having a cavity formed therein and a cleaning fluid reservoir formed in a bottom portion of the cavity that is configured to undergo vibrational movement. At least one ultraviolet radiation source can be located about the interior surfaces of the cavity and the cleaning fluid reservoir to direct ultraviolet light to the razor blade assembly simultaneously or in conjunction with the cleaning action provided by the vibrational cleaning fluid in response to the assembly substantially immersed or partially immersed in the fluid.

In one embodiment, the housing can include a container having a cavity formed therein and a cleaning fluid reservoir formed in a bottom portion of the cavity. The container can have a surface with an opening into the cavity for insertion of the razor blade assembly, wherein the opening is configured to limit placement of the razor blade assembly within the cavity to a suspended state held over the cleaning fluid reservoir without immersion therein. In one embodiment, the housing can include at least one ultraviolet radiation source that directs ultraviolet radiation to the razor blade assembly, and a cleaning fluid nozzle that operates in conjunction with the source to direct pressurized cleaning fluid from the cleaning fluid reservoir to the razor blade assembly. A filter system can filter cleaning fluid from the cleaning fluid reservoir and a pumping system can pump filtered cleaning fluid from the filter system to the cleaning fluid nozzle.

The interior surface of the housing of the various embodiments can include an ultraviolet transparent material. In one embodiment, the ultraviolet transparent material can be formed between the ultraviolet radiation source and the razor blade assembly. The ultraviolet transparent material can include one of an ultraviolet transparent fluoropolymer film, an ultraviolet transparent glass or an ultraviolet transparent crystal. In one embodiment, the interior surface of the housing can include a reflective layer to promote recycling of ultraviolet light emitted towards the razor blade assembly. Other layers that can be applied to the interior surface of the housing can include a light diffusive layer and a fluorescent layer.

The shaving razor cleaning unit of the various embodiments can include a control unit to initiate a cleaning treatment of the razor blade assembly with at least one ultraviolet radiation source in response to the razor blade assembly being placed within the housing. In one embodiment, the control unit can specify various operating parameters for the cleaning treatment of the razor blade assembly. The operating parameters can include a cleaning treatment time that ultraviolet radiation is directed towards the front portion and/or the rear portion of the bladed member, a dosage of ultraviolet radiation delivered by the ultraviolet radiation source, a power setting for operating the ultraviolet radiation source, and a maximum operating temperature.

The control unit can include or operate in conjunction with other components to facilitate the ultraviolet cleaning treatment. For example, a timer can be set in accordance with the specified cleaning treatment time in order to ensure that the ultraviolet radiation source delivers a sufficient dosage for the corresponding cleaning treatment being performed on the razor blade assembly, e.g., disinfection, sterilization, sanitization, and/or the like. An input component can permit a user to adjust at least one of the operating parameters and an output component can indicate status information of the cleaning treatment (e.g., on, off, cleaned, needs cleaning, etc.).

At least one sensor can be configured to monitor one of the operating parameters during the cleaning treatment and provide signals thereof to the control unit, so that the control unit can control operation of the cleaning treatment as a function of the signals received from the sensor. In addition, a power supply can provide power to all of the components of the ultraviolet-based razor shaving cleaning unit to facilitate the cleaning treatment of a razor blade assembly.

A first aspect of the invention provides a system, comprising: a housing to receive a razor blade assembly having at least one bladed member; at least one ultraviolet radiation source located within the housing to emit ultraviolet radiation towards a front portion and a rear portion of the bladed member; and a control unit to initiate a cleaning treatment of the razor blade assembly with the at least one ultraviolet radiation source in response to the razor blade assembly being placed within the housing, the control unit specifying a plurality of operating parameters for the cleaning treatment of the razor blade assembly, the plurality of operating parameters including a cleaning treatment time that the ultraviolet radiation source emits the ultraviolet radiation towards the front portion and the rear portion of the bladed member, a dosage of ultraviolet radiation delivered by the ultraviolet radiation source, a power setting for operating the ultraviolet radiation source, and a maximum operating temperature.

A second aspect of the invention provides a shaving razor assembly, comprising: a razor handle; a razor blade unit having at least one bladed member for shaving a surface that is detachably coupled to the razor handle; and a shaving razor cleaning cover unit removably coupled to the razor blade unit that is configured to provide an ultraviolet cleaning treatment to the razor blade unit, wherein the shaving razor cleaning unit comprises a bifurcated cap having a main body portion, a first bifurcated element and a second bifurcated element opposing the first bifurcated element and separated therefrom, the first bifurcated element and the second bifurcated element each having a first end rigidly fixed to the main body portion and a second end that is flexibly unattached, the main body portion, the first bifurcated element and the second bifurcated element forming an opening that is configured to receive the razor blade unit.

A third aspect of the invention provides a shaving razor cleaning unit, comprising: a housing having a container with a surface opening into a cavity formed in the container; a cleaning fluid reservoir formed in a bottom portion of the cavity, wherein the opening in the container is configured to limit placement of the razor blade assembly within the cavity to a suspended state held over the cleaning fluid reservoir without immersion therein; at least one ultraviolet radiation source located about an interior surface of the housing to direct ultraviolet radiation towards the razor blade assembly; and a cleaning fluid nozzle operating in conjunction with the ultraviolet radiation source to direct pressurized cleaning fluid from the cleaning fluid reservoir to the razor blade assembly.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 2 shows a schematic of a shaving razor cleaning unit having an open-ended container with a shaving razor placed therein according to an embodiment.

FIG. 3 shows a schematic of a shaving razor cleaning unit having an open-ended container with bifurcated elements to secure a shaving razor according to an embodiment.

FIGS. 9A-9C show schematic views of shaving razor cleaning cover unit for a shaving razor having a shaving razor assembly according to embodiments.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
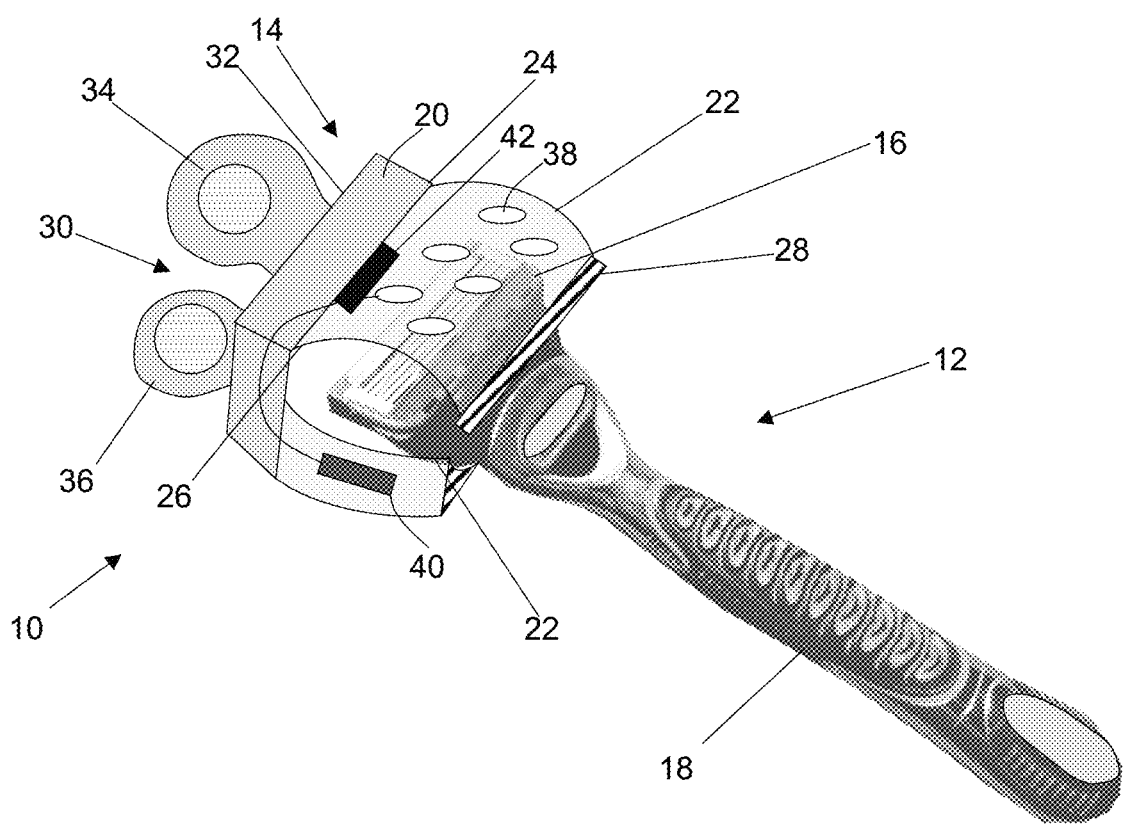
FIG. 1 shows a schematic of a shaving razor cleaning unit with a shaving razor according to an embodiment.

As indicated above, aspects of the invention are directed to ultraviolet cleaning or treating (e.g., disinfecting, sterilizing, sanitizing) of shaving razors to remove bacteria, viruses, germs, and the like. These aspects utilize a shaving razor cleaning unit or system having a housing and at least one ultraviolet radiation source to direct ultraviolet radiation to a razor blade assembly having at least one bladed member for treatment thereof. The shaving razor cleaning unit can operate with wet shaving razors that utilize safety razors, razor cartridges, razor blades, straight razors, and/or the like, and dry shaving razors that can include, but are not limited to, electric razors, electric hair trimmers for beards, mustaches, ears, eyebrows and other body parts where it may be desirable to trim hair. In other aspects, the shaving razor cleaning unit can be integrated with a wet shaving razor assembly or a dry shaving razor assembly to provide a cleaning to the bladed member(s) associated with each modality after use thereof. Thorough cleaning of shaving razors with the shaving razor cleaning unit can lead to reduced infections, and life prolongation of the razors.

The various shaving razor cleaning units described herein and their respective configurations can include a number of components described herein in more detail, some of which may be optional, that facilitate an ultraviolet cleaning treatment of a shaving razor. The modalities used with the various shaving razor cleaning units including its respective components can include any now known or later developed approaches that incorporate the concepts and configurations of the embodiments described below in more detail.

As used herein, a cleaning treatment of a shaving razor can entail sanitizing, disinfecting, and/or sterilizing a shaving razor. Sanitizing generally means reducing the number of bacterial contaminants to a predetermined safe level. Disinfecting generally means destroying pathogenic and other types of microorganisms, while sterilizing can be more extensive in that it kills all microbial forms and/or include destroying the ability of the microbial forms to reproduce.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 to about 280 nm provides the highest germicidal effectiveness and viral disinfection. While susceptibility to ultraviolet radiation varies, exposure to ultraviolet energy in the above range for about 20 to about 34 milliwatt-seconds/cm$^2$ is adequate to deactivate approximately 99 percent of the pathogens.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through.

The description that follows may use other terminology herein for the purpose of describing particular embodiments only and is not intended to be limiting of the disclosure. For example, unless otherwise noted, the term "set" means one or more (i.e., at least one) and the phrase "any solution" means any now known or later developed solution. The singular forms "a," "an," and "the" include the plural forms as well, unless the context clearly indicates otherwise. It will be further understood that the terms "comprises", "comprising", "includes", "including", "has", "have", and "having"

when used in this specification, specify the presence of stated features, integers, steps, operations, elements, and/or components, but do not preclude the presence or addition of one or more other features, integers, steps, operations, elements, components, and/or groups thereof.

Turning to the drawings, FIG. 1 shows a schematic of a shaving razor cleaning unit 10 with a shaving razor 12 according to an embodiment. The shaving razor cleaning unit 10 can include a housing 14 to receive a razor blade assembly 16 having at least one bladed member from the shaving razor 12. In the embodiment illustrated in FIG. 1, the razor blade assembly 16 is a razor blade cartridge having a number of bladed members (e.g., a multi-bladed razor) attached to a razor handle 18 of the shaving razor 12, however, it is understood that other types of razors (e.g., safety razors, straight edge razors, and the like) are suitable for use with the shaving razor cleaning unit 10. The housing 14 can include a base member 20 and a pair of opposing grasping members 22 extending outward from a first side 24 of the base member 20. Each grasping member can have a first end 26 fixedly attached to the first side 24 of the base member 20 and a second end 28 unattached to the base member 20. The first end 26 of each grasping member 22 can pivotally attach to opposite ends of the first side 24 of the base member 20. The second end 28 of each grasping member 22 can converge towards one another.

The housing 14 can further include a clamping handle 30 attached to a second side 32 of the base member 20. The clamping handle 30 can have a first clamping handle portion 34 and a second clamping portion 36 that actuate movement of the second ends 28 of the grasping member 22 from a converging position to a diverging open position configured to receive the razor blade assembly 16. For example, a user can apply pressure to the first clamping handle portion 34 and the second clamping portion 36 that causes the second ends 28 of the grasping member 22 to move apart in opposing directions so that the razor blade assembly 16 can be placed between the grasping members 22. The second ends 28 of the grasping member 22 can grip and cover the razor blade assembly 16 in response to the actuating movement being removed from the first clamping handle portion 34 and the second clamping portion 36. For example, the user can remove the pressure from the first clamping handle portion 34 and the second clamping portion 36, allowing the second ends 28 of the grasping member 22 to move towards the razor blade assembly 16 so that the grasping members apply a gripping force that secures the shaving razor 12 to the shaving razor cleaning unit 10.

Housing 14 is illustrative of only one type of enclosure that can be placed around a typical mechanical razor blade, however, it is understood that other clippable housing enclosures that can be placed around a shaving razor blade are within the scope of this embodiment. For example, a clippable housing having an elastic mechanical device such as a spring can be used to close over a razor blade by applying a mechanical force.

In one embodiment, at least one ultraviolet radiation source 38 can be located within the housing 14 to emit ultraviolet radiation towards a front portion of the bladed member(s) of the razor blade assembly 16. For example, as shown in FIG. 1, one or both of the grasping members 22 can include one or more ultraviolet radiation sources 38. The grasping member 22 of the housing 14 of the shaving razor cleaning unit 10 that faces the front portion of the bladed members of the razor blade assembly 16 can include the ultraviolet radiation sources 38, while the grasping member 22 that faces the rear portion of the bladed members can have at least one ultraviolet radiation source 38 in an optional embodiment. In this manner, the front portion of the bladed members of the razor blade assembly 16 that are used for shaving a surface can receive an ultraviolet treatment, while the rear portion of the bladed member that receives a lesser amount of shaving debris can also receive an ultraviolet treatment to minimize any buildup of germs and bacteria that have the potential to lead to adverse health concerns.

Each ultraviolet radiation source 38 can be located within the housing 14, adhering to an inner surface or integrated therein. For example, in FIG. 1, the ultraviolet radiation sources 38 can be integrated with the grasping members 22 or located on an interior surface such that the emitting faces of the sources are oriented to emit ultraviolet light towards the front portion of the razor blade assembly 16 and optionally the rear portion to effectuate a cleaning treatment. The set of ultraviolet radiation sources 38 can comprise any combination of one or more ultraviolet radiation emitters. Examples of ultraviolet radiation emitters can include, but are not limited to, high intensity ultraviolet lamps (e.g., high intensity mercury lamps), discharge lamps, UV LEDs, super luminescent LEDs, laser diodes, and/or the like. In one embodiment, the set of ultraviolet radiation sources 38 can include a set of LEDs manufactured with one or more layers of materials selected from the group-III nitride material system (e.g., $Al_xIn_yGa_{1-X-Y}N$, where $0 \le x$, $y \le 1$, and $x+y \le 1$ and/or alloys thereof). Additionally, the set of ultraviolet radiation sources 38 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a waveguide, a plurality of ultraviolet fibers, each of which terminates at an opening, a diffuser, a light guiding layer, a light diffusing layer, and/or the like.

It is understood that the number of ultraviolet radiation sources 38 illustrated in FIG. 1 and the other embodiments depicted in the other figures is only illustrative. Those skilled in the art will appreciate any number of ultraviolet radiation sources 38 may be located within the housing 14. For example, the grasping member 22 that faces the front portion of the bladed member of the razor blade assembly 16 can have a number of sources that extend over the length of each bladed member in the assembly and only one ultraviolet radiation source 38 located at a central portion of the grasping member 22 that faces the rear portion of the assembly.

In order to effectuate a cleaning treatment of the bladed member(s) of the razor blade assembly 16, the ultraviolet radiation sources 38 can be configured to be operated at a number of wavelengths. For example, in one embodiment, the ultraviolet radiation sources 38 can be configured to operate at a wavelength that ranges from about 250 nm to about 310 nm. In another embodiment, the ultraviolet radiation sources 38 can be configured to operate concurrently at multiple wavelengths. For example, at least one ultraviolet radiation source 38 can operate at a first wavelength with a peak wavelength of 280 nm, while at least one other source can operate a second wavelength at peak wavelength of 250 nm, with each having a wavelength range of about 20 nm. Emission of ultraviolet light within this wavelength range for a predetermined time period is sufficient to effectively clean the razor blade assembly 16 from a germicidal effectiveness point of view.

It is understood that the ultraviolet radiation sources 38 can be configured to function in other coordinated manners. For example, the ultraviolet radiation sources 38 can operate at the same wavelengths and intensities for the same duration, or the sources can operate at different wavelengths and intensity for varying durations. In one embodiment, a first set of ultraviolet radiation sources 38 can operate at a target wavelength and intensity that is designed for the disinfection of one type of bacteria and/or viruses, while a second set of ultraviolet radiation sources 38 can operate at a different target wavelength and intensity that is designed for disinfection of a different type of bacteria and/or viruses.

The interior surface of the housing 14 can comprise an ultraviolet transparent material formed between the ultraviolet radiation sources 38 and the razor blade assembly 16. For example, the interior surfaces of the base member 20 and the pair of opposing grasping members 22 that form the part of the housing 14 in the shaving razor cleaning unit 10 that are configured to secure the razor blade assembly 16 can include an ultraviolet transparent material. In one embodiment, the ultraviolet transparent material can include an ultraviolet transparent fluoropolymer film. Examples of an ultraviolet transparent fluoropolymer material can include, but are not limited to, fluorinated ethylene propylene co-polymer (EFEP), fluorinated ethylene propylene (FEP), polytetrafluoroethylene (PTFE, such as Teflon®), ethylene chlorotrifluoroethylene (ECTFE), polychlorotrifluoroethylene (PCTFE), perfluoroalkoxy (PFA), polyvinylidene fluoride (PVDF), ethylene tetrafluoroethylene (ETFE), tetrafluoroethylene hexafluoropropylene vinylidene fluoride co-polymer (THV), low density polyethylene (LDPE), perfluoro methyl alkoxy (MFA), and/or the like. While primarily described in conjunction with fluoropolymers, it is understood that other comparable materials can be utilized such as polylactide (PLA), fused silica, sapphire, THE, ultraviolet transparent glass, ultraviolet transparent crystal, and/or the like. Other transparent materials that can formed on the interior surfaces of the housing 14 can include, but are not limited to, $SiO_2$, $TiO_2$, $Al_2O_3$, $CaF_2$, $MgF_2$.

In order to recycle or recirculate the ultraviolet radiation emitted from the ultraviolet radiation sources 38, all of the inner surfaces of the housing 14 or at least a portion (e.g., at least 5% of the entire surface area) can have an ultraviolet reflective layer. For example, in FIG. 1, the interior surfaces of the base member 20 and the pair of opposing grasping members 22 that form the part of the housing 14 in the shaving razor cleaning unit 10 that are configured to secure the razor blade assembly 16 can include an ultraviolet reflective layer. An ultraviolet reflective layer with a reflection coefficient of at least 50% will enable recycling of the ultraviolet radiation generation from the ultraviolet radiation sources 38. In one embodiment, the ultraviolet reflective layer can include polished aluminum, PTFE (e.g., Teflon@), expanding polytetrafluoroethylene (ePTFE), ETFE or combinations thereof. In another embodiment, the ultraviolet reflective layer can include a diffusive ultraviolet reflective layer. The diffusive ultraviolet reflective layer can include a coating or thin film of a fluoropolymer. Examples of a fluoropolymer that are suitable as an ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like.

Other materials can be applied to the interior surfaces of the housing 14 or at least portions thereof. For example, a fluorescent material can be incorporated into the ultraviolet transparent layer in order to emit visible light under the application of targeted ultraviolet radiation. Examples of fluorescent material that can be used with the shaving razor cleaning unit 10 can include, but are not limited to, phosphor.

In another embodiment, the ultraviolet transparent layer can incorporate diffusive elements capable of producing diffusive illumination in order to diffuse ultraviolet illumination over surfaces requiring disinfection. Examples of diffusive elements that can be incorporated with the ultraviolet transparent layer can include, but are not limited to, fluoropolymers, fluoropolymer powders, $Al_2O_3$ powders, $SiO_2$ powders, and/or the like. In one embodiment, the diffusive illumination of the diffusive elements can be at least 10% Lambertian.

A control unit 40 can initiate a cleaning treatment of the razor blade assembly 16 with the ultraviolet radiation sources 38 in response to the razor blade assembly being placed within the housing 14. For example, in FIG. 1, the control unit 40 can initiate the cleaning treatment once the razor blade assembly 16 is placed between the grasping members 22 and secured thereby. The control unit 40 can specify a plurality of operating parameters for the cleaning treatment of the razor blade assembly 16. The plurality of operating parameters can include, but are not limited to, a cleaning treatment time that the ultraviolet radiation sources 38 emit the ultraviolet radiation towards the front portion and/or the rear portion of the bladed member(s) of the razor blade assembly 16, a dosage of ultraviolet radiation delivered by the ultraviolet radiation sources 38, a power setting for operating the ultraviolet radiation sources, and a maximum operating temperature for the ultraviolet cleaning treatment. It is understood that these operating parameters are illustrative of some of the parameters that can be set by the control unit 40 and is not meant to be limiting as other parameters exist which may be specified such as a wavelength of the ultraviolet light used for disinfection, and/or the like.

The shaving razor cleaning unit 10 can include other components in addition to the control unit 40 to effectuate a cleaning treatment of the shaving razor 12. For example, as shown in FIG. 1, at least one sensor 42 can be configured to monitor one of the operating parameters during the cleaning treatment and to provide signals thereof to the control unit 40. The control unit 40 can control the operation of the cleaning treatment as a function of the signals received from the sensor 42. For clarity FIG. 1 shows only one sensor 42, however, it is understood that more than one sensor can be used, and that more than one type of sensor can be used. Examples of sensors that can be used include, but are not limited to, bacterial fluorescence sensors, visible light sensors, temperature sensors, pressure sensors, chemical sensors, radiation sensors (e.g., an ultraviolet dose counter or meter), a visible camera, etc.

In one embodiment, a bacterial fluorescence sensor can detect the amount or regions where there is a presence of bacteria, germs, viruses, and/or the like, which is present on the bladed members of the shaving razor assembly 16. For example, the bacterial fluorescence sensor can generate signals representative of the condition of the bladed members with respect to the amount of bacteria, germs, viruses, and the like, and sends those signals to the control unit 40. The control unit 40 can determine whether a cleaning treatment is necessary as a function of the feedback signals provided by the bacterial fluorescence sensor using any solution and direct the ultraviolet radiation source 38 to direct radiation to the applicable area with appropriate intensity. In one embodiment, the control unit 40 can activate the operation of the ultraviolet radiation sources 38 in response to determining that the bladed members have an amount of bacteria, germs, viruses, and/or the like, which exceeds a predetermined threshold, and thus, requires a cleaning treatment. Activating the operation of the ultraviolet radiation sources 38 by the control unit 40 can include specifying the aforementioned operating parameters. In addition, the control unit 40 can the signals from the sensor 42 to adjust a current treatment cycle.

In another example, a pressure sensor, a proximity sensor (e.g., a capacitance, optical, magnet proximity sensor), or the like can be used to detect when the shaving razor is secured with the housing 14 of the shaving razor cleaning unit 10. In this manner, the control unit 10 can use signals generated from the sensor 42 to determine whether the shaving razor assembly 16 is positioned properly for receiving a cleaning treatment.

Any of the aforementioned sensors can be deployed along with the ultraviolet radiation sources 38 in the shaving razor cleaning unit 10 in any desired configuration. For example, the sensor(s) 42 can be interspersed with the ultraviolet radiation sources 38 or separated from each other.

The control unit 40 can include a timer with switches and/or the like, to manage the duration that the ultraviolet radiation sources 38 are on for a particular cleaning treatment, and ensure that radiation is applied to a particular surface of the shaving razor assembly 16 for that duration (e.g., a dosage timer). In one embodiment, the control unit 40 operating in conjunction with the timer can manage the amount of time that the ultraviolet radiation sources 38 radiate in the UV-C range versus the UV-B range. The duration and frequency treatment that the ultraviolet radiation sources 38 are utilized can depend on detected condition signals provided to the control unit 40 by any of the sensors 42 (e.g., the blade contamination determined either from fluorescent feedback or from visual feedback), as well as any other predetermined treatment factors such as the length that a particular shaving razor has been used, areas of the body where it is in use, and whether a set predefined treatment schedule is being followed.

During operation of a cleaning treatment, the control unit 40 can be used to control at least one of a plurality of predetermined ultraviolet radiation characteristics associated with the ultraviolet radiation emitted from the ultraviolet radiation sources 38. The predetermined ultraviolet radiation characteristics that can be controlled by the control unit 40 can include wavelengths, intensities, and durations and/or the like. In one embodiment, the control unit 40 can control the wavelength of ultraviolet radiation and intensity spatially over the bladed member of the shaving razor assembly 16. As an example, the control unit 40 can control the ultraviolet radiation sources 38 to operate at a target wavelength and intensity for a duration that is designed for the disinfection of bacteria and/or viruses on a surface of the blades member of the shaving razor assembly 16.

In an embodiment, the control unit 40 can determine the target intensity of the radiation based on an amount of time since a previous cleaning has been performed. For example, the control unit 40 can implement an algorithm in which a minimum ultraviolet intensity is utilized when a previous cleaning was performed within a certain period of time, and the intensity is increased to a maximum intensity, which is utilized when the previous cleaning was performed over a maximum period of time. The intensity range can be determined based on attributes of the ultraviolet radiation sources 38. The target intensity can be incremented in steps or continuously over the range of times corresponding to the varying intensities. The range of times can be determined based on, for example, feedback data acquired regarding a severity of contamination typical for a period of time. In an embodiment, the control unit 40 can generate a warning signal for presentation to a user when the time period since a previous cleaning has exceeded a maximum recommended time (e.g., time period corresponding to the maximum ultraviolet radiation). The warning signal can be generated using any type of output device including, for example, a vibration device, a visible light (e.g., flashing), an auditory signal generated by a speaker, and/or the like.

In addition, during the operation of the cleaning treatment, the control unit 40 can be used to turn on or off the ultraviolet radiation sources 38 dependent upon the detected conditions provided by the sensors 42. Also, the control unit 40 can be used to adjust one or more of the ultraviolet radiation characteristics based on the conditions detected by the sensors 42. For example, the control unit 40 can use the signals from a bacterial fluorescence sensor that are representative of the amount of bacteria, germs, viruses, and/or the like, present on a surface of the razor to adjust the intensity, the wavelength, the duration and or the pattern of the ultraviolet radiation emitted from any of the ultraviolet radiation sources 38. In another embodiment, the control unit 40 can be configured to interrupt the operation of the ultraviolet radiation sources 38 in response to receiving temperature signals from a temperature sensor and determining that the temperature of the cleaning treatment has exceeded the maximum temperature. The control unit 40 can resume the cleaning treatment after a predetermined cooling time has elapsed.

The control unit 40 can also include a wireless transmitter and receiver that is configured to communicate with a remote location via Wi-Fi, BLUETOOTH, and/or the like. As used herein, a remote location is a location that is apart from the ultraviolet cleaning treatment system. For example, a remote computer can be used to transmit operational instructions to the wireless transmitter and receiver. The operational instructions can be used to program functions performed and managed by the control unit 40. In another embodiment, the wireless transmitter and receiver can transmit cleaning treatment results, data from the sensors 42 to the remote computer, to facilitate maintenance and diagnostic operations on the ultraviolet cleaning treatment system.

The control unit 40 can include an input component and an output component to allow a user to interact with the shaving razor cleaning unit 10 and to receive information regarding the treatment. In one embodiment, the input component can permit a user to adjust at least one of the aforementioned plurality of operating parameters. This can include making adjustments during the cleaning treatment operation and/or prior to initiating a treatment. In one embodiment, the input component can include a set of buttons and/or a touch screen to enable a user to specify various input selections regarding the operating parameters as well as the cleaning treatment. In one embodiment, the output component can include a visual display for providing status information on the cleaning treatment (e.g., time remaining, the presence of bacteria, viruses, germs or the like), an indication that a cleaning treatment is recommended, an indication that the device has been sterilized, disinfected, sanitized, an indication that the device has been disinfected, sanitized, an indication after its last use, a simple visual indicator that displays whether a cleaning treatment is underway (e.g., an illuminated light) or if the treatment is over (e.g., absence of an illuminated light).

The shaving razor cleaning unit 10 can further include a power source that is configured to power each of the ultraviolet radiation sources 38, the control unit 40 and the sensors 42. In one embodiment, the power source can take the form of one or more batteries, a vibration power generator that can generate power based on magnetic inducted oscillations or stresses developed on a piezoelectric crystal. In another embodiment, the power source can include a super capacitor that is rechargeable. Other power components that are suitable for use as the power source for the shaving razor cleaning unit 10 can include a mechanical energy to electrical energy converter such as a piezoelectric crystal, and a rechargeable device.

Figure 10A:
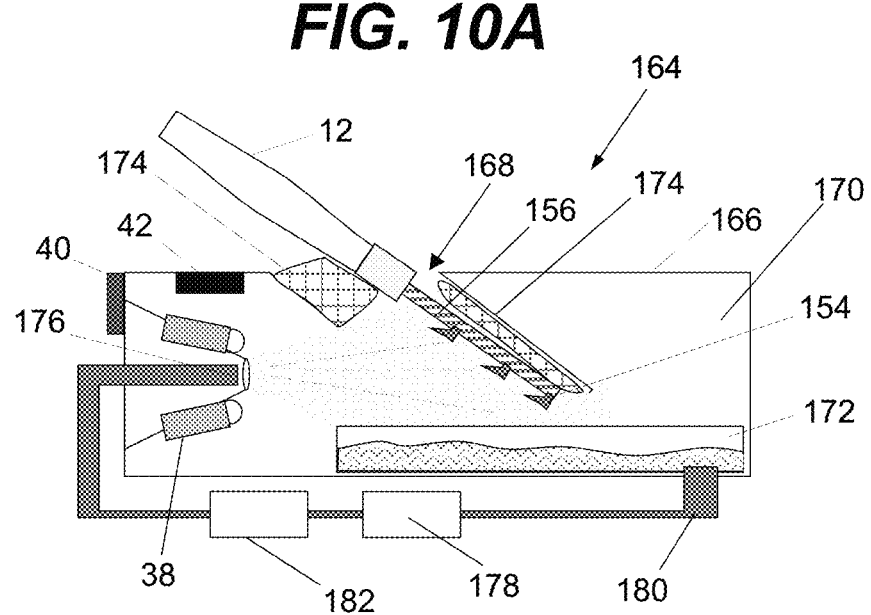
FIGS. 10A-10B show schematic views of a shaving razor cleaning unit having a container with an opening into a cavity that limits placement of a shaving razor to a suspended state held over a cleaning fluid reservoir according to embodiments.
Figure 10B:
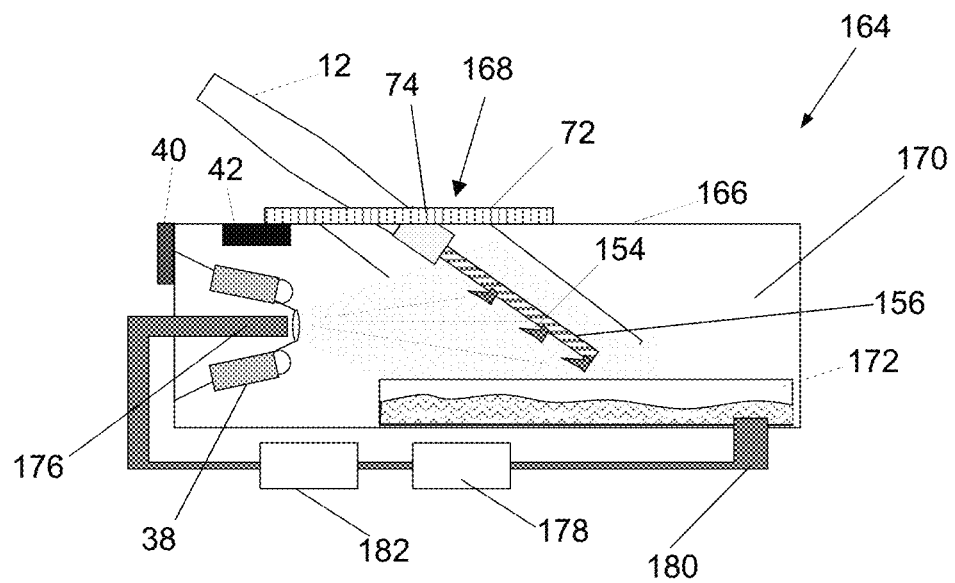
Figure 11:
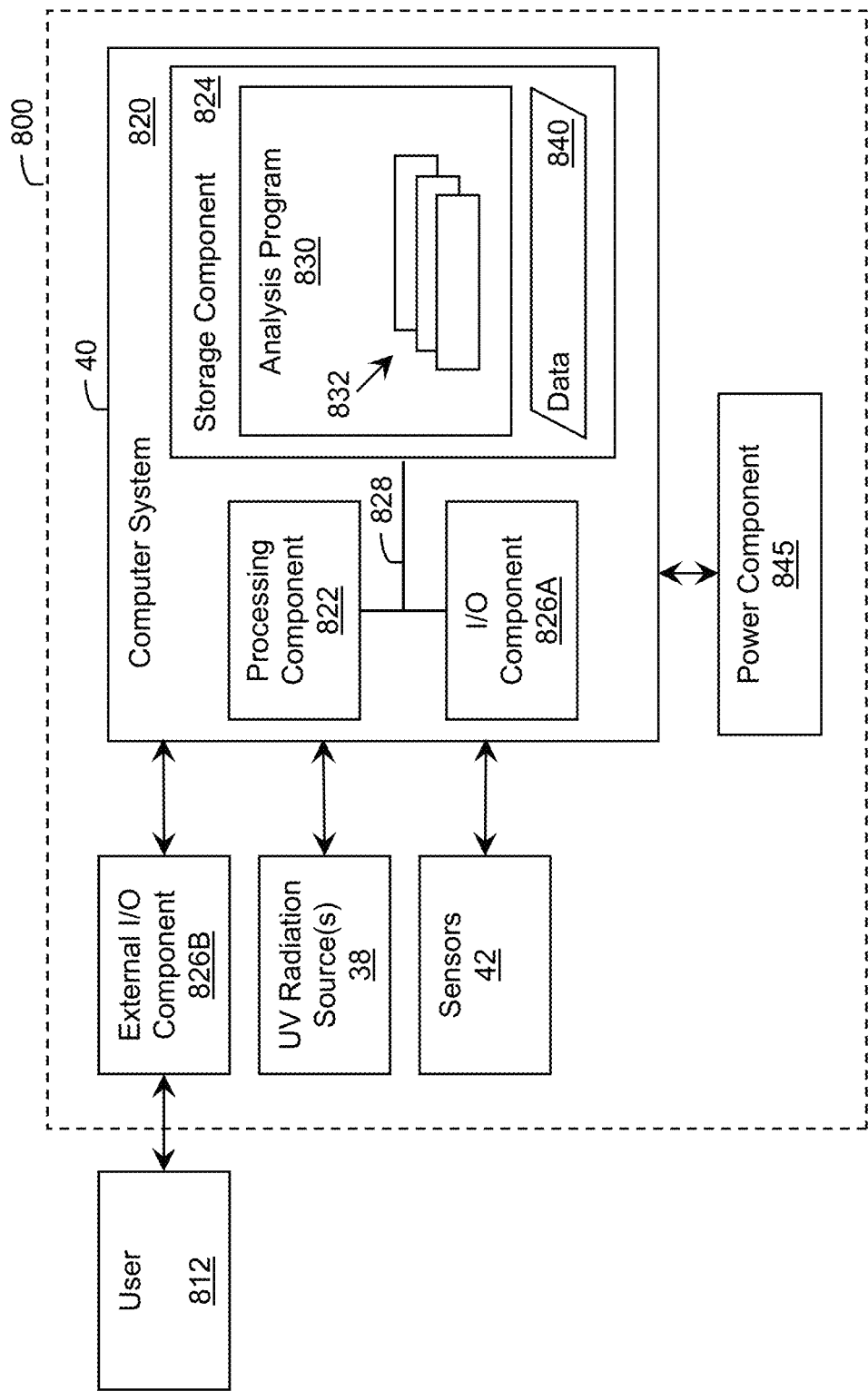
FIG. 11 shows a schematic of a shaving razor cleaning unit that can be implemented with any of the embodiments depicted in FIGS. 1-10 according to an embodiment.
Figure 12:
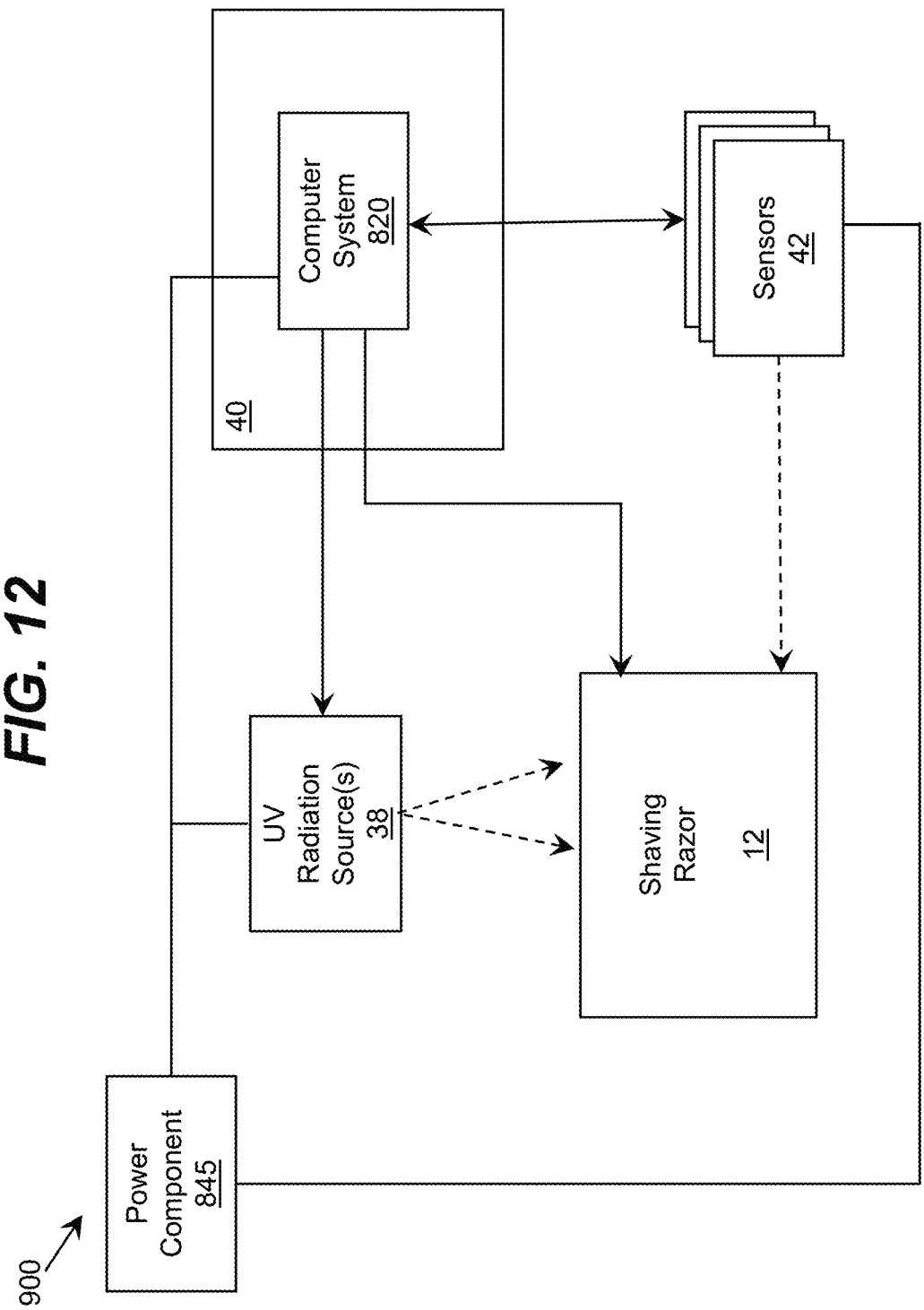
FIG. 12 shows a schematic of an illustrative environment in which the shaving razor cleaning unit depicted in FIG. 11 can be used to facilitate a cleaning treatment of a shaving razor according to an embodiment.

The aforementioned components of the shaving razor cleaning unit 10 are illustrated in FIGS. 11-12 and discussed further with regard to these figures. These components of the ultraviolet cleaning treatment system are suitable for use with the various other embodiments described herein with respect to FIGS. 2-10. It is understood that the functions of these components can vary and will depend on the type of shaving razor that is to undergo a cleaning treatment. Thus, the functions described are only illustrative of examples of particular functions and operations to be performed and are not meant to be limiting to the embodiment of FIG. 1 as well as to an ultraviolet cleaning treatment system used in conjunction with the embodiments pertaining to FIGS. 2-10.

FIG. 2 shows a schematic of a shaving razor cleaning unit 44 having an open-ended container 46 with a shaving razor 12 placed therein according to an embodiment. A cavity 48 can be formed in the container 46 to receive the shaving razor 12 including the razor blade assembly 16. As shown in FIG. 2, the interior walls of the container 46 can substantially surround the razor blade assembly 16 including its bladed members and a portion of the razor handle 18 upon placement of the shaving razor in the cavity 48 of the container 46. It is understood that the size of the container 46 and the cavity 48 and the degree to which these components consume the shaving razor 12 including the razor blade assembly 16 and the razor handle 18 can vary, and the design depicted in FIG. 2 is not intended to be limiting to the scope of this embodiment. Those skilled in the art will appreciate that a number of open-ended containers can be designed with an opening like that depicted in FIG. 2 that allows for a tight holding of a shaving razor therein, and are within the scope of this embodiment.

In this configuration, at least one ultraviolet radiation source 38 can be integrated with the container 46 to direct ultraviolet radiation to the bladed members of the razor blade assembly 16 and the portion of the razor handle 18 that is covered within the cavity 48. In one embodiment, a multitude of ultraviolet radiation sources 38 can be located along various portions of the container 46 to direct ultraviolet radiation towards the frontal portion of the bladed member that are used to shave a surface and the rear portion of the blades that can collect shaving debris. Any of the aforementioned layers and/or materials that can facilitate ultraviolet cleaning of the shaving razor 12 like the ultraviolet transparent layer, the diffusive layer, the diffusive elements, the reflective layer, the fluorescent material and light guiding components can be used in this embodiment as well as others described herein. In addition, at least one sensor 42 can operate in conjunction with the ultraviolet radiation source 38 in order to obtain various measurements regarding the ultraviolet cleaning of the shaving razor 12. The control unit 40 can use the measurements obtained by the sensors 42 to control the operating parameters of the ultraviolet radiation sources 38 and the overall cleaning treatment applied to the shaving razor 12.

In one embodiment, the shaving razor cleaning unit 44 with its open-ended container 46 can take the form of a table standing unit, and wherein the shaving razor 12 can be inserted into the cavity 48 from the top portion of the container. FIG. 2 also shows that an input/output (I/O) component can be incorporated with the control unit 40. In one embodiment, the input/output (I/O) component can include a set of buttons or a touch screen operated by software that facilitates control of ultraviolet cleaning treatments. For example, the software can be configured to optimize the ultraviolet radiation emitted towards the razor blade assembly 16 within the container 46 based on the visible or fluorescent characteristics of the bladed members. The I/O component can also provide a display of information regarding the treatment to the user via a display and/or LEDs.

FIG. 3 shows a schematic of a shaving razor cleaning unit 50 having an open-ended container 52 with bifurcated elements 54 to secure a shaving razor (not depicted) according to an embodiment. The open-ended container 52 with bifurcated elements 54 can take the form of a bifurcated cap that is configured for insertion of any one of a variety of mechanical razor blade assemblies. In one embodiment, the bifurcated cap container 52 with bifurcated elements 54 can include a main body portion 56, a first bifurcated element 58, and a second bifurcated element 60 opposing the first bifurcated element and separated therefrom. The first bifurcated element 58 and the second bifurcated element 60 can each have a first end rigidly 62 fixed to the main body portion 56 and a second end 64 that is flexibly unattached. In this manner, the main body portion 56, the first bifurcated element 58 and the second bifurcated element 60 can form an opening 66 that is configured to receive the razor blade assembly.

The open-ended container 52 with bifurcated elements 54 can include at least one ultraviolet radiation source 38 that the control unit 40 can instruct to emit ultraviolet radiation towards a razor blade assembly stored therein. In one embodiment, the first bifurcated element 58 can include ultraviolet radiation sources 38 configured to direct ultraviolet radiation to the front portion of the bladed members of the razor blade assembly. Although not shown in FIG. 3 for sake of clarity, it is understood that the second bifurcated element 60 can have at least one ultraviolet radiation source 38 as can an interior surface of the main body portion 56. Other components not depicted in FIG. 3 can include at least one sensor 42 that can detect conditions associated with the razor blade assembly and the ultraviolet cleaning treatment process. The inner surfaces of the main body portion 56, the first bifurcated element 58 and the second bifurcated element 60 can have all or portions thereof with at least one of a light diffusive layer, an ultraviolet transparent layer, a reflective layer, a fluorescent layer and the like.

Figure 4:
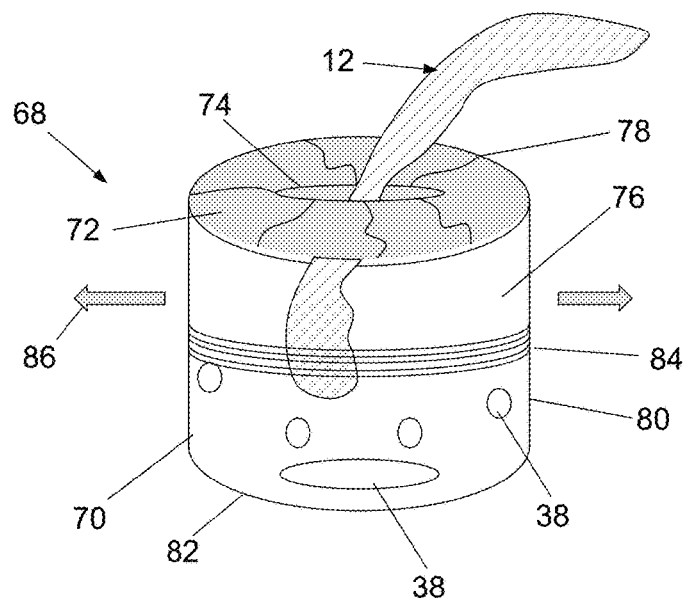
FIG. 4 shows a schematic of a shaving razor cleaning unit having a container with a membrane at one end with a flexible opening insertable into a cavity that is configured to receive a shaving razor according to an embodiment.

FIG. 4 shows a schematic of a shaving razor cleaning unit 68 having a container 70 with a membrane 72 at one end with a flexible opening 74 insertable into a cavity 76 that is configured to receive a shaving razor 12 and substantially surround the razor blade member upon placement therein. In one embodiment, the top of the membrane 72 can have a set of cuts 78 that are radially oriented from the opening 74 to the periphery of the container 70. The opening 74 and the set of cuts 78 in the top of the membrane 72 allow an object such as a shaving razor to be inserted therein and irradiated by a set of ultraviolet radiation sources 38 located about the container 70 that can operate in conjunction with a control unit and at least one sensor (both not depicted for clarity). In one embodiment, the ultraviolet radiation sources 38 can be located on the inner side walls 80 of the container 70. It is understood that the number and location of the ultraviolet radiation sources 38 can vary. In one embodiment, the inner surface of a bottom portion 82 of the container 70 can have an ultraviolet radiation sensor 38. Further, it is understood that the inner side walls 80, the bottom portion 82 of the container 70, and/or the inner side of the membrane 72 can have at least one of a light diffusive layer, an ultraviolet transparent layer, a reflective layer, a fluorescent layer or the like, to promote the ultraviolet treatment of the object placed therein.

In one embodiment, the container 70 can be made from any appropriate material that absorbs ultraviolet radiation including, but not limited to, glass, metal, plastic, etc., while the membrane 72 can be made from a material that includes, but is not limited to, rubber, plastic, and/or the like. The container 70 can also be configured as a container with a set of threads 84 that split the container into two halves when unthreaded. In this manner, a threaded container allows a user to open the container for cleaning and maintaining purposes.

In one embodiment, the container 70 can have an ultrasonic generator (not shown) used in conjunction with a cleaning fluid placed in the container to complement the cleaning of the object placed therein by the ultrasonic radiation source 38. An ultrasonic generator can cause movement of the cleaning fluid in the container 70 in several directions as indicated by movement arrows 86, which can help dislodge particles from the object such as shaving debris from a shaving razor. The cleaning fluid can include, but is not limited to, alcohol, chlorine dioxide, peroxyacetic acid, and/or the like. In one embodiment, the cleaning fluid can include a hot gas of sufficient flow for thorough cleaning of the bladed members of a razor blade assembly. For example, a hot gas such as hot air can be used to clean the bladed members.

Figure 5:
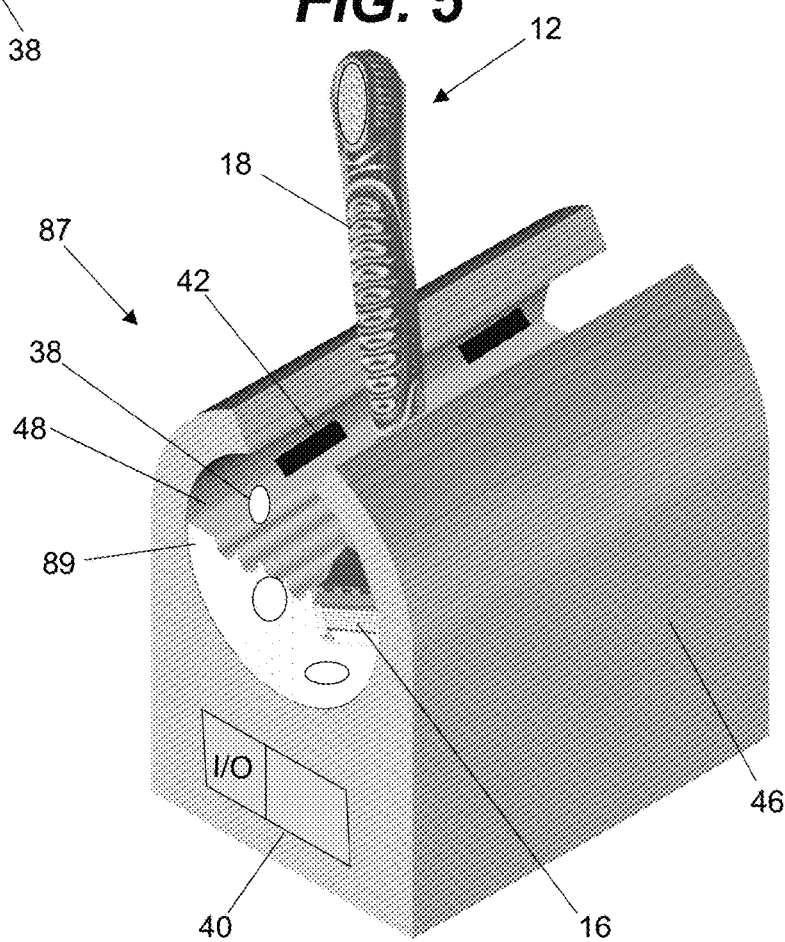
FIG. 5 shows a schematic of a shaving razor cleaning unit having an open-ended container and a cleaning fluid reservoir with a shaving razor placed therein according to an embodiment.

FIG. 5 shows a schematic of a shaving razor cleaning unit 87 having a cleaning fluid reservoir 89 that can be used in conjunction with at least one ultraviolet radiation source 38 to clean a shaving razor 12. The shaving razor cleaning unit 87 of FIG. 5 is similar to the one depicted in FIG. 2, except that a portion of the open-ended container 46 includes the cleaning fluid reservoir 89 containing cleaning fluid with the shaving razor placed therein according to an embodiment. The cleaning fluid used as the cleaning fluid reservoir 89 can contain any of the above-mentioned cleaning fluids. In one embodiment, the shaving razor cleaning unit 87 can utilize an ultrasonic generator to cause movement of the cleaning fluid in the container 46, which can help dislodge shaving debris from the shaving razor. In one embodiment, instead of using a reservoir, the cleaning fluid can be delivered to the container to flow through the cavity 48. For example, it is possible to have the open-ended container 46 to have side ends that are open such that the cleaning fluid can flow through one end to the other. In this manner, a razor assembly 16 placed in the cavity 48 of the container 46 can be subjected to a flow of cleaning fluid that is sufficient to dislodge shaving debris from the bladed members or chemically interact with the bladed members for disinfection.

The use of the cleaning fluid with or without the ultrasonic generator can complement the cleaning of the shaving razor 12 by the ultraviolet radiation sources 38. For example, the control unit 38 can instruct the ultraviolet radiation sources 38 to deliver a targeted amount of radiation for a certain duration to the razor assembly 16 of the shaving razor 12. The control unit 38 can further instruct the ultrasonic generator to create a vibrational movement of the cleaning fluid from the cleaning fluid reservoir 89. The control unit 38 can coordinate operation of the ultraviolet radiation sources 38 and the ultrasonic generator to operate simultaneously or at different times. In one embodiment, the input/output (I/O) component of the control unit 40 can be used by a user to select what type modality is preferred for a given cleaning treatment. It is understood that the I/O component can be used by the user to input one of a number of process settings. At least one sensor 42 can monitor the processes performed by the ultraviolet radiation sources 38 and the ultrasonic generator and provide feedback to the control unit 40. The control unit 40 can use this feedback to adjust any of the operating parameters associated with the ultraviolet radiation sources 38 and the ultrasonic generator during the cleaning process. Also, the I/O component of the control unit 40 can be used to provide results of the cleaning treatment process to the user. Besides result information, the I/O component can have a display that indicates the status of the cleaning treatment process and the shaving razor cleaning unit (e.g., ON, OFF).

Figure 6A:
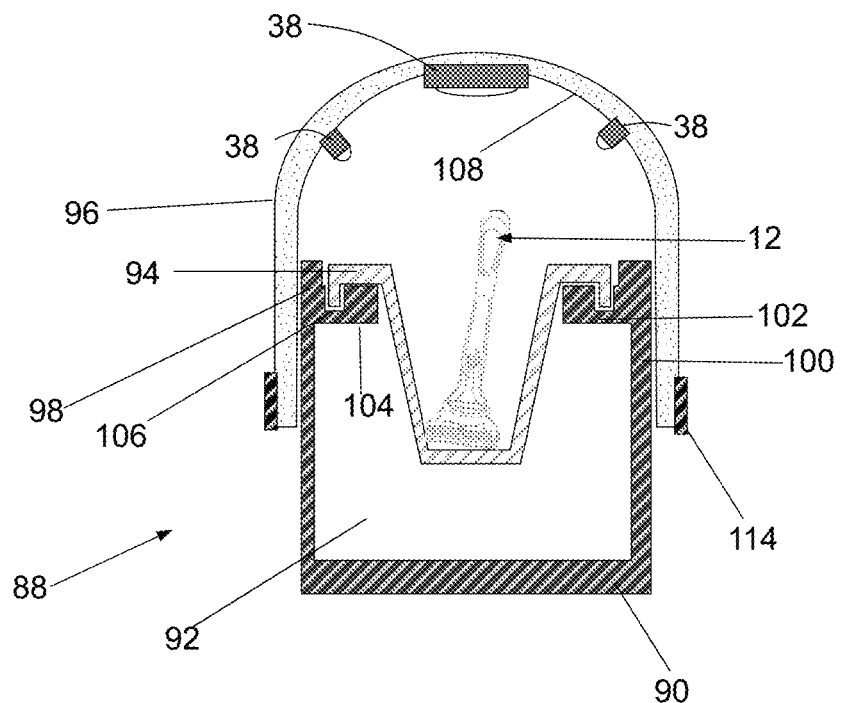
FIGS. 6A-6B show schematics of a shaving razor cleaning unit including a container having a cavity formed therein, a removable platform suspended in the container that is configured to support a shaving razor, and a removable cover that fastens to the container and provides access to the cavity and the platform upon removal thereof according to various embodiments.
Figure 6B:
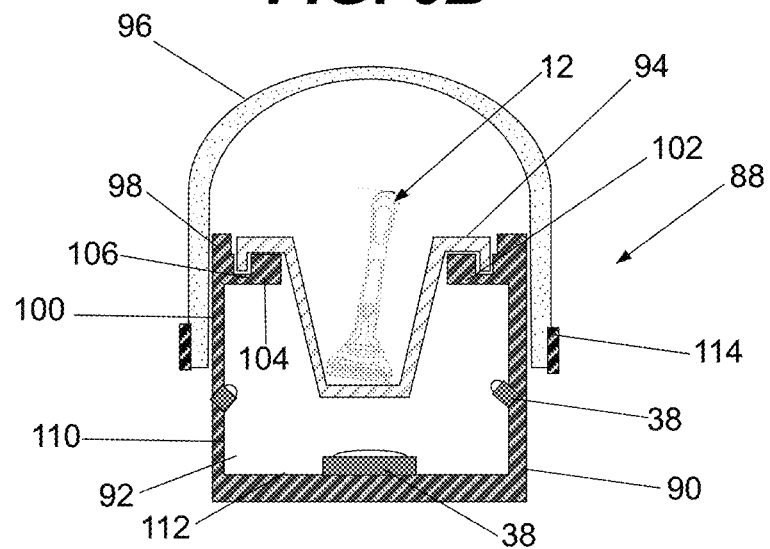

FIGS. 6A-6B show schematics of a shaving razor cleaning unit 88 including a container 90 having a cavity 92 formed therein, with a removable platform 94 suspended in the container that is configured to support a shaving razor 12, and a removable cover 96 for placement over the container and preventing the escape of ultraviolet radiation from the container. In one embodiment, as shown in FIGS. 6A-6B, the container 90 includes a top edge portion 98 that projects inward towards the cavity 92 away from a portion of the cover 96 that extends along a side region 100 of the container. The top edge portion 98 abuts an inner rim 102 of the container 90. The inner rim 102 can have a lip support 104 and an indentation 106 to securely support the platform 94 upon placement in the container 90. In this manner, the platform 94 can suspend the razor blade 12 within the cavity 92 of the container 90, so that the razor blade does not touch the container walls. This is advantageous for hygienic purposes, wherein the shaving razor cleaning unit 88 can be shared between multiple people or installed in a place like a hotel facility.

As shown in FIGS. 6A-6B, the platform 94 can be shaped to be complementary to mate with the lip support 104 and the indentation 106 of the inner rim 102 of the container 90. In one embodiment, the platform 94 can be formed from a disposable material such as for example a paper material. Depending on the location of the ultraviolet sources 38, which as shown in FIG. 6A can be located on the inner walls 108 of the cover 96, or as shown in FIG. 6B, can be along the inner walls of the container 90 including side walls 110 and a bottom wall 112, the material used for the platform 94 can include a paper material with a surface comprising a reflective foil for reflecting ultraviolet radiation. It is understood that the inner walls 108 of the cover 96 and/or the side walls 110 and bottom wall 112 of the container 90 can have other materials that promote the recycling of ultraviolet radiation such as for example, but not including, at least one of a light diffusive layer, an ultraviolet transparent layer, a fluorescent layer and/or the like.

The cover 96 can be configured with a fastener mechanism 114 to aid in securing the cover to the side walls 110 of the container 90, while unfastening the fastener mechanism enables access to the cavity 92 and the platform 94 and the shaving razor 12. In this manner, shaving razor 12 can be inserted to and removed from the platform 94 for a cleaning treatment or upon completion of a treatment by the ultraviolet radiation sources 38. Although not shown in FIGS. 6A-6B, the shaving razor cleaning unit 88 can include a control unit with an input component and an output component that allows a user to control the treatment and be apprised of the conditions and results of the treatment per data obtain by sensors used in conjunction with the ultraviolet radiation sources and the control unit.

The fastener mechanism 114 can include any of a number of fastening solutions that can act as a locking or securing mechanism for fastening the cover 96 to the container. In one embodiment, the fastener mechanism 114 can include a magnetic coupling that can magnetically attach to a metal strip on the side walls 110 of the container 90. Other fastener mechanisms can include, but are not limited to, buckles, clips, tabs, hook and loop fasteners, mechanical fasteners (e.g., threaded connections), friction type fastening devices placed between two surfaces, etc.

Both the container 90 and the cover 96 can be made from a variety of materials. For example, the container 90 and the cover 96 can be made from materials that can include, but are not limited to, aluminum, plastic, glass, etc.

Figure 7:
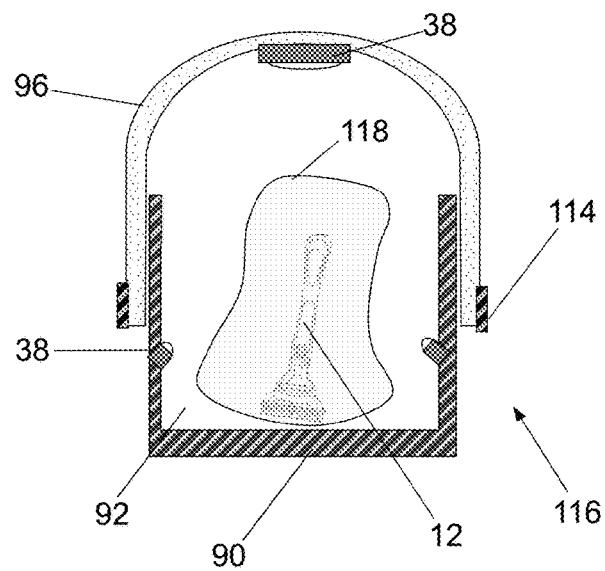
FIG. 7 shows a schematic of a shaving razor cleaning unit including a container having a cavity formed therein and a removable cover that fastens to the container for placement of an ultraviolet transparent receptacle that can hold a shaving razor according to an embodiment.

FIG. 7 shows a schematic of a shaving razor cleaning unit 116 including a container 90 having a cavity 92 formed therein and a removable cover 96 that fastens to the container for placement of an ultraviolet transparent receptacle 118 that can hold a shaving razor 12 according to an embodiment. The embodiment depicted in FIG. 7 is similar to those shown in FIGS. 6A-6B, however, the container 90 in this embodiment does not support a removable platform for supporting the shaving razor 12. Instead, the container 90 is configured without a top edge portion and an inner rim that projects inward towards the cavity 92. In this manner, the ultraviolet transparent receptacle 118 with the shaving razor 12 placed therein can be easily inserted into the cavity 92 of the container 90. In one embodiment, the ultraviolet transparent receptacle 118 can include a flexible pouch having an opening to a reflective inner surface that is at least 30% reflective with a reflection coefficient that is at least 50%, and that receives the shaving razor 12. The ultraviolet transparent receptacle 118 can further include an overlapping opening cover which can cover the opening in response to the shaving razor 12 inserted therein to prevent ultraviolet radiation that is emitted from the ultraviolet radiation sources 38 from escaping the receptacle 118. This adds another safeguard to the cover 96 which can prevent the radiation from escaping the container 90 during a cleaning treatment of the shaving razor 12. In one embodiment, the ultraviolet transparent receptacle 118 can be made from a material that includes any of the aforementioned fluoropolymers.

In one embodiment, the ultraviolet transparent receptacle 118 can include a mesh with thin and rare threads such that it does not significantly obstruct ultraviolet radiation. It is understood, that an ultraviolet transparent receptacle 118 formed from a mesh bag could be used in the embodiments depicted in FIGS. 6A-6B, such that it could be placed on the platform 94 and suspended within the container 90 such that the shaving razor does not touch the container walls. Furthermore, it is understood that the ultraviolet transparent receptacle 118 can be used to hold other smaller-sized items that may have the need for an ultraviolet treatment. For example, the ultraviolet transparent receptacle 118 and the container 90 can be used to treat a multitude of toiletry items such as for example, toothbrushes, brushes, combs, soap trays, and the like.

Figure 8:
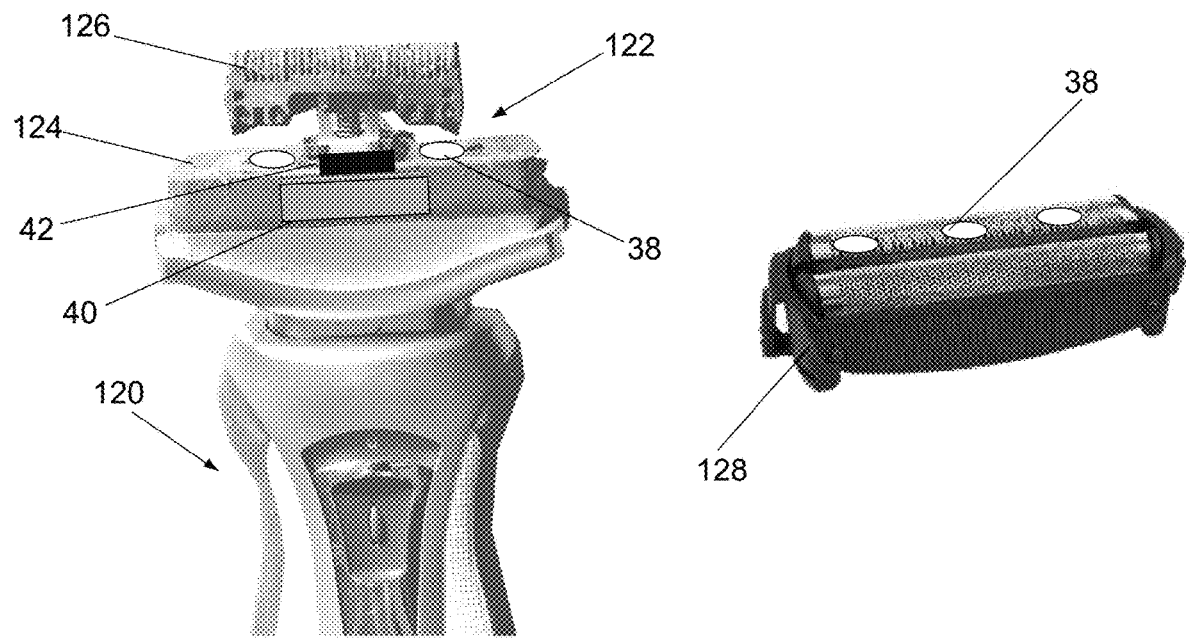
FIG. 8 shows a schematic of an electric razor having an integrated shaving razor cleaning unit according to an embodiment.

FIG. 8 shows a schematic of an electric razor 120 having an integrated shaving razor cleaning unit 122 according to an embodiment. In this embodiment, at least one ultraviolet radiation source 38 and a sensor 42 can be located on a platform header 124 of the electric razor 120 underneath a cutting block 126 in which a foil 128 containing blade members is positioned there over. Ultraviolet radiation sources 38 can also be formed on the top portion of the foil to irradiate the cutting surfaces of the blade members of the foil 38. Having the ultraviolet radiation sources 38 located at positions over and under the blade members of the foil 38 can provide cleaning treatment that covers a larger area of the foil. It is understood that the ultraviolet radiation sources can be located either over or underneath the blade members and that this embodiment is not meant to be limited to the configuration depicted in FIG. 8. It is further understood that this embodiment is also applicable to electric razors that do not employ a foil of blade members. For example, it is possible to fit ultraviolet radiation sources 38 and sensors 42 with electric razors that use rotary blade members.

The cleaning treatment rendered to the bladed members of the electric razor 120 can be effectuated by a control unit 40 in the aforementioned manner. In one embodiment, the control unit can be integrated on the platform header 124. However, it is understood that the control unit can be located on other portions of the electric razor such as for example as the main body of the razor. Furthermore, the control unit 40 can be configured with an input and output component that facilitates user input and output pertaining to the cleaning treatment of the electric razor 120 (e.g., ultraviolet source settings, information on the disinfection results of the treatment).

Figure 9A:
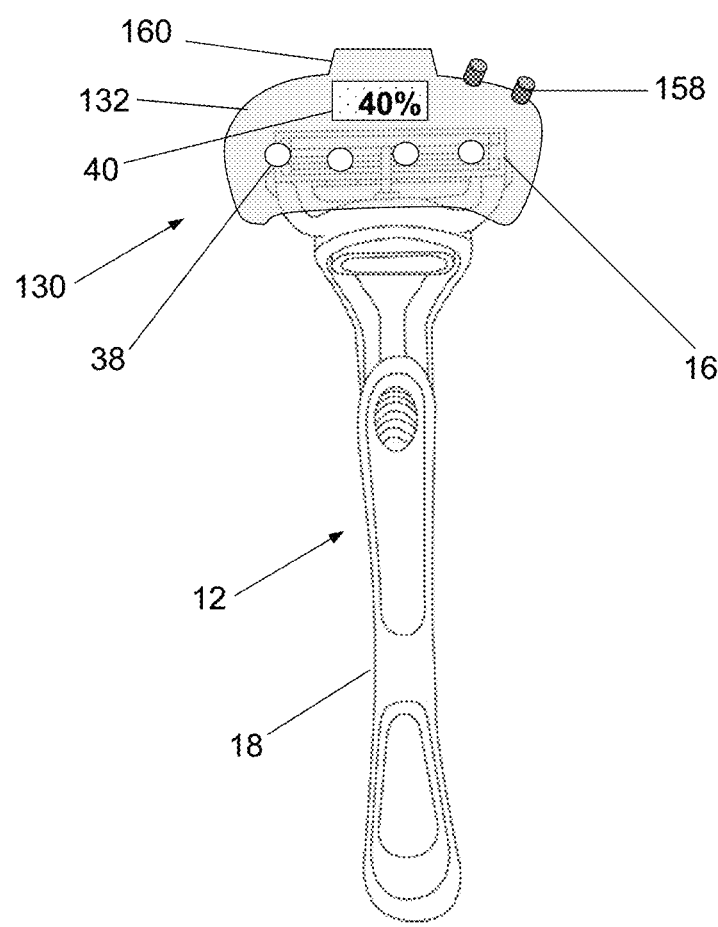

FIGS. 9A-9C show schematic views of shaving razor cleaning cover unit 130 for a shaving razor 12 having a shaving razor assembly 16 in the form of a razor blade unit having at least one bladed member 154 supported by a blade holding member 156, and a razor handle 18 that can be detachably coupled to the razor blade unit. The shaving razor cleaning cover unit 130 can be removably coupled to the razor blade unit to provide an ultraviolet cleaning treatment to the razor blade unit with at least one ultraviolet radiation source 38.

In one embodiment, the shaving razor cleaning unit 130 can include a bifurcated cap 132 having a main body portion 134, a first bifurcated element 136 and a second bifurcated element 138 opposing the first bifurcated element and separated therefrom. The first bifurcated element 136 and the second bifurcated element 138 can each having a first end 140 rigidly fixed to the main body portion 134 and a second end 142 that is flexibly unattached. In this configuration, the main body portion 134, the first bifurcated element 136 and the second bifurcated element 138 form an opening 144 that is configured to receive the razor blade unit. As a result, the bifurcated cap 132 can form a partially flexible housing capable of small deflections as shown by arrows 143 for the insertion and removal of the razor blade assembly.

As shown in FIGS. 9B-9C, the first bifurcated element 136 can include a set of ultraviolet radiation sources 38 configured to direct ultraviolet radiation to the bladed members 154 of the razor blade unit. In one embodiment, the ultraviolet radiation sources 38 incorporated in the first bifurcated element 136 can be configured to emit ultraviolet radiation to the top portion of the bladed members 154. It is understood that the second bifurcated element 138 can be configured to have the ultraviolet radiation sources 38 in place of, or in addition to those disposed with the first bifurcated element 136.

The interior surfaces of the main body portion 134, the first bifurcated element 136 and the second bifurcated element 138 that face the opening 144 can have films, layers or coatings of material that can facilitate recycling or recirculation of ultraviolet radiation that is emitted from the ultraviolet radiation sources 38 that can be located within the first bifurcated element 136 along with one or more sensors 42 in order to increase the efficiency of a cleaning treatment applied to the razor blade unit. For example, the interior surfaces of one or more of the main body portion 134, the first bifurcated element 136 and the second bifurcated element 138 can have an ultraviolet reflective layer that is reflective to at least 30%. Other examples can include, but are not limited to, a light diffusive layer, a fluorescent layer, and ultraviolet transparent layer.

In one embodiment, an interior surface of the first bifurcated element 136 can include an ultraviolet transparent material that is formed between the ultraviolet radiation sources 38 and the bladed member(s) of the razor blade unit. For example, the ultraviolet transparent material can include one of an ultraviolet transparent fluoropolymer film such as those noted above, an ultraviolet transparent glass or an ultraviolet transparent crystal. It is understood that the second bifurcated element 138 could be applied with the ultraviolet transparent material for embodiments in which the ultraviolet radiation sources are disposed therein.

In another embodiment, the interior surface of the first bifurcated element 136 can be shaped with ultraviolet transparent forms 145 to improve light guiding and radiating of the bladed members with the ultraviolet radiation generated from the ultraviolet radiation sources 38. For example, the ultraviolet transparent forms 145 can take the form of projections that are shaped into the walls of the first bifurcated element 136. It is understood that the second bifurcated element 138 could also be shaped with the ultraviolet transparent forms 145 for embodiments in which the ultraviolet radiation sources are disposed therein.

In one embodiment, as depicted in FIG. 9B, the first bifurcated element 136 can include a light diffusive layer 146 configured to eliminate the razor blades with sufficient uniformity. The light diffusive layer 146 can comprise a laminate structure of sublayers, with at least some layers comprising diffusive elements, fibers or grains. These diffusive elements, fibers or grains can include, but are not limited to, $SiO_2$, $TiO_2$, $Al_2O_3$, $CaF_2$, $MgF_2$, and/or a transparent fluoropolymer.

In one embodiment, as depicted in FIG. 9C, the first bifurcated element 136 can be configured to include a set of photo-catalyst domains 148 configured to improve the disinfection. The photo-catalyst domains 148 can include material such as, but not limited to, $TiO_2$. Use of the photo-catalyst domains 148 to clean the razor blade unit can serve as a supplemental modality to the cleaning treatment provided by the ultraviolet radiation sources 38.

In one embodiment, as depicted in FIG. 9C, the second bifurcated element 138 can include a fluorescent material 150 incorporated into a transparent layer 152. The fluorescent material 150 can emit visible light under the application of a target ultraviolet radiation. In this manner, the fluorescent material 150 can be used as an indication of the presence of ultraviolet radiation. Examples of fluorescent material include, but are not limited to, phosphor. In addition, the fluorescence sensor 42 can be used to acquire data corresponding to a fluorescence signal coming from the blade surface. The control unit 40, shown in FIG. 9B, could determine the amount or presence of bacteria, germs, viruses, and/or the like, based on data acquired by the fluorescence sensor 42 and control the cleaning treatment in a manner to eradicate it from the bladed members.

FIGS. 9A-9C show various embodiments of features associated with the control unit 40 that can be incorporated into the shaving razor cleaning cover unit 130. In one embodiment, the shaving razor cleaning cover unit 130 can have a display screen to display information regarding the cleaning treatment to the user, and to also allow the user to input various settings for the treatment of the shaving razor 12. For example, in FIG. 9A, the display screen is depicted as part of the control unit 40 that as mentioned above can include an I/O component that enables user input as well as the generation of output to the user. The screen can be incorporated with the bifurcated cap 132. In one embodiment, the screen be placed with one of the bifurcated elements 136 and 138, however, it is understood that it could incorporated with the main body portion 134, and even possibly along the razor handle 18.

The display screen can be used to display a multitude of information. For example, FIG. 9A shows the display screen displaying the percentage of time left in the ultraviolet cleaning treatment (e.g., 40%). In addition to the timing of radiation (e.g., the time required to finish the treatment, the time that the unit has been engaged in radiation), the display screen can display other information which can include, but is not limited to, the intensity of ultraviolet radiation, the dosage of radiation used for disinfection, the status of the cleaning treatment (e.g., On/Off), the type of germs or bacteria detected, whether a cleaning or disinfection treatment is necessary, whether the razor is scheduled for predetermined treatment, etc.

In one embodiment, the display screen can be configured as a touch screen. In this manner, the user can be given the option to input information to the shaving razor cleaning unit 130 via the control unit 40. For example, the user can input settings for controlling the treatment, such as the type of ultraviolet radiation, the dosage of the radiation, the intensity of the radiation, the wavelength of the radiation, etc. It is understood that other modalities can be used to input control settings to the shaving razor cleaning unit 130. For example, input buttons 158 placed on the bifurcated cap 132 can be used to input control settings such as the type of ultraviolet radiation used for the treatment, the dosage of the radiation, the intensity of the radiation, the wavelength of the radiation, etc.

The shaving razor cleaning unit 130 can further include a power source that is configured to power each of the ultraviolet radiation sources 38, the control unit 40 and the sensors 42. The power source can include, but is not limited to, batteries, an accumulator, a piezoelectric crystal, and a super capacitor. In one embodiment, the bifurcated cap 132 of the shaving razor cleaning unit 130 can be a rechargeable device. For example, the bifurcated cap 132 can have an electrical connection 160 formed in the main body portion 134 as depicted in FIGS. 9A-9C that enables charging of the shaving razor cleaning unit 130 from an electrical outlet. In one embodiment, the electrical connection 160 can take the form of a USB port or any other power electrical port that can facilitate charging from an electrical outlet. Alternatively, the shaving razor cleaning unit 130 can be charged wirelessly. For example, the main body portion 134 of the bifurcated cap 132 can be configured to have wireless communication capability to effectuate the wireless charging option. As shown in FIG. 9B, shaving razor cleaning unit 130 can have an indicator light 162 such as for example an LED, to indicate the status of the power source (e.g., charging, needs charging) and the operation of the unit (e.g., On/Off).

FIGS. 10A-10B show schematic views of a shaving razor cleaning unit 164 having a container 166 with an opening 168 into a cavity 170 that limits placement of a shaving razor 12 to a suspended state held over a cleaning fluid reservoir 172 according to embodiments. As shown in FIGS. 10A-10B, the opening 168 can be formed in a top surface of the container 166, while the cleaning fluid reservoir 172 can be formed in a bottom portion of the cavity 170 within the container 166. The opening 168 can be formed in a central region of the top surface of the container 166, while the cleaning fluid reservoir 172 can occupy a limited region of the bottom portion of the cavity 170. It is understood that the location of both the opening 168 and the cleaning fluid reservoir 172 and the extent of space that each occupies with regard to the top surface and cavity of the container, respectively, is only illustrative of possible locations and sizes, and is not meant to limit the scope of this embodiment.

The opening 168 in the container 166 can be configured to limit placement of the razor blade assembly of the shaving razor 12 within the cavity to a suspended state held over the cleaning fluid reservoir 172 without immersion therein. In one embodiment, as depicted in FIG. 10A, a set of rubber friction elements 174 can be located about the opening. For example, a larger rubber friction element 174 can be placed at an angle on the top surface of the container 166 at a portion of the opening 168, while a smaller set of rubber friction elements 174 can be positioned in the opening. In this manner, the bladed members 154 on the blade supporting member 156 of the razor blade assembly of the razor blade 12 can be positioned and supported in the opening 168 at an angle within the cavity 170 facing a fluid stream of cleaning fluid generated from a cleaning fluid nozzle 176, and ultraviolet radiation emitted from at least one ultraviolet radiation source 38. This configuration allows the bladed members to receive sufficient coverage of cleaning fluid provided by the cleaning fluid nozzle 176 and radiation emitted from the ultraviolet radiation sources 38.

In another embodiment as depicted in FIG. 10B, the opening 168 in the container 166 can be configured as a membrane 72 with a flexible opening 74 and a set of cuts insertable into a cavity 170 that is configured to receive the shaving razor 12. The membrane with the flexible opening 74 and the set of cuts can function to limit placement of the bladed members 154 of razor blade assembly of the shaving razor 12 within the cavity 170 to a suspended state held over the cleaning fluid reservoir 172 without immersion therein. Like the embodiment depicted in FIG. 10A, the bladed members 154 of the razor blade assembly of the razor blade 12 can be positioned and supported in the opening 168 at an angle for receiving the cleaning fluid from the cleaning fluid nozzle 176 and the ultraviolet radiation from the ultraviolet radiation source 38, and thus providing optimal cleaning.

FIGS. 10A-10B both show that the shaving razor cleaning unit 164 can include a filter system 178 to filter or recycle cleaning fluid supplied from the cleaning fluid reservoir 172 by channel 180, and a pumping system 182 to pump filtered cleaning fluid from the filter system to the cleaning fluid nozzle 176. Any of the aforementioned cleaning fluids are suitable for use as a cleaning agent with the cleaning fluid reservoir 172. In one embodiment, the cleaning fluid can be water which the cleaning fluid nozzle 176 can direct as a pressurized fluid to the bladed members 154. Delivering the pressurized stream of water from the cleaning fluid nozzle 176 to the bladed members 154, which are disposed at a specific angle within the cavity 170 to the nozzle and the ultraviolet sources 38 provides effective removal of shaving debris and any germs, bacterial, and the like from the blades.

It is understood that other cleaning agents are suitable for use in this embodiment and that the shaving razor cleaning unit 164 is not meant to be limited to agents that are fluids. For example, a high velocity of air flow can be directed from the cleaning fluid nozzle 176 onto the bladed members 154.

As shown in FIGS. 10A-10B, the shaving razor cleaning unit 164 can be configured with a control unit 40 to initiate a cleaning treatment of the bladed members 154 with the at least one ultraviolet radiation source 38 and the cleaning fluid from the cleaning fluid reservoir 172 that is directed to the blades. The control unit can specify the operating parameters for the cleaning treatment of the bladed members 154. These operating parameters can include any of the aforementioned parameters associated with the ultraviolet source 38, parameters set specifically for directing a pressurized stream of cleaning fluid from cleaning fluid reservoir 172 to the bladed members 154 by the cleaning fluid nozzle 176. The nozzle operating parameters can include, but are not limited to, a cleaning fluid treatment time that the cleaning fluid nozzle 176 directs cleaning fluid to the bladed members 154, a flow or power setting for delivering the pressurized fluid, and a patterned-type of spray delivered by the nozzle. In addition, the control unit 40 can specify the order of operation of the ultraviolet radiation sources 38 and the pressurized stream from the cleaning fluid nozzle 176. For example, the control unit 40 can specify the ultraviolet radiation sources 38 operate simultaneously with the cleaning fluid nozzle 176, before the nozzle operation, or after it. In one embodiment, the ultraviolet radiation sources 38 can be configured to operate during and after high pressure cleaning by the cleaning fluid nozzle 176.

The control unit 40 can monitor and control the operation of both the ultraviolet radiation sources 38 and the cleaning fluid nozzle 176 based on data from one or more sensors 42 located about the cavity 170 in the container 166. Any of the aforementioned sensors 42 are suitable for use with this embodiment. The control unit 40 can control the operation of the cleaning treatment provided by the ultraviolet radiation sources 38 and the cleaning fluid nozzle 176 as a function of the signals received from the sensor 42. For example, the operation of the high pressure cleaning provided by the cleaning fluid nozzle 176 can be contingent on the amount of debris on the bladed members 154 or the amount that has been debrided, as measured by one or more sensors 42 located about the cavity 170. Once the there is no more debris coming from the bladed members 154, the control unit 40 can stop the operation of the cleaning fluid nozzle 176 and/or the ultraviolet radiation sources 38, and indicate the completion of the cleaning cycle.

It is understood that there are multiple possible configurations for implementing the ultraviolet radiation sources 38, the sensors 42, the cleaning fluid nozzle 176, the cleaning fluid reservoir 172, the channel 180, the filter system 178, the pumping system 182, and the control unit 40 within the shaving razor cleaning unit 164. For example, the ultraviolet radiation sources 38 can be placed elsewhere in the container 166 to provide adequate exposure of the bladed members 154 to the ultraviolet radiation. In one embodiment, the filter system 178 can be located about the container 166 in a position that is easily accessible for cleaning. Also, the cleaning fluid reservoir 172 can have an inlet/outlet to add more fluid or to remove the used fluid from the reservoir.

FIG. 11 shows a schematic of a shaving razor cleaning unit 800 that can be implemented with any of the embodiment described herein. In this embodiment, the shaving razor cleaning unit 800 is shown including the ultraviolet radiation sources 38 (UV radiation source(s)) and the sensors 42 for the purposes of illustrating the interaction of all of the components that are used to provide a cleaning treatment to a shaving razor.

As depicted in FIG. 11 and described herein, the shaving razor cleaning unit 800 can include a control unit 40. In one embodiment, the control unit 40 can be implemented as a computer system 820 including an analysis program 830, which makes the computer system 820 operable to manage the ultraviolet radiation sources 38 and the sensors 42 in the manner described herein. In particular, the analysis program 830 can enable the computer system 820 to operate the ultraviolet radiation sources 38 to generate and direct ultraviolet radiation towards a surface of the bladed members of the shaving razor and process data corresponding to one or more attributes regarding the device, which can be acquired by the sensors 42, and/or an ultraviolet radiation history stored as data 840. The computer system 820 can individually control each ultraviolet radiation source 38 and sensor 42 and/or control two or more of the ultraviolet radiation sources and the sensors as a group. Furthermore, the ultraviolet radiation sources 38 can emit ultraviolet radiation of substantially the same wavelength or of multiple distinct wavelengths.

In an embodiment, during an initial period of operation, the computer system 820 can acquire data from at least one of the sensors 42 regarding one or more attributes of the shaving razor and generate data 840 for further processing. The data 840 can include information regarding a presence of biological activity (e.g., microorganisms, viruses, bacteria, and/or the like) on a surface of the shaving razor, a frequency of usage of the shaving razor, a disinfection schedule history for the razor, an amount of radiation (e.g., ultraviolet, infrared, visible, and/or microwave) detected, and/or the like. The computer system 820 can use the data 840 to control one or more aspects of the ultraviolet radiation generated by the ultraviolet radiation source(s) 38 during a cleaning treatment.

Furthermore, one or more aspects of the operation of the ultraviolet radiation sources 38 can be controlled or adjusted by a user 812 via an external interface I/O component 826B. The external interface I/O component 826B can be located on the exterior of any of the aforementioned shaving razor cleaning units, and used to allow the user 812 to selectively turn on/off the ultraviolet radiation sources 38. However, it is understood that, in order to turn on the ultraviolet radiation sources 38, the computer system 820 can first determine that the shaving razor has been securely placed within a housing, receptacle, container, or the like (e.g., via data acquired by one or more sensors 42).

The external interface I/O component 826B can include, for example, a touch screen that can selectively display user interface controls, such as control dials, which can enable the user 812 to adjust one or more of: an intensity, scheduling, and/or other operational properties of the set of ultraviolet radiation sources 38 (e.g., operating parameters, radiation characteristics). In an embodiment, the external interface I/O component 826B could conceivably include a keyboard, a plurality of buttons, a joystick-like control mechanism, and/or the like, which can enable the user 812 to control one or more aspects of the operation of the set of ultraviolet radiation sources 38. The external interface I/O component 826B also can include any combination of various output devices (e.g., an LED, a visual display), which can be operated by the computer system 820 to provide status information pertaining to a cleaning treatment of a shaving razor for use by the user 812. For example, the external interface I/O component 826B can include one or more LEDs for emitting a visual light for the user 812, e.g., to indicate a status of the cleaning treatment. In an embodiment, the external interface I/O component 826B can include a speaker for providing an alarm (e.g., an auditory signal), e.g., for signaling that ultraviolet radiation is being generated or that a cleaning treatment has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors. To this extent, in other embodiments, the functionality provided by the computer system 820 and the analysis program 830 can be at least partially be implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of the cleaning treatment. Illustrative aspects of the invention are further described in conjunction with the computer system 820. However, it is understood that the functionality described in conjunction therewith can be implemented by any type of monitoring and/or control system.

Regardless, when the computer system 820 includes multiple computing devices, the computing devices can communicate over any type of communications link. Furthermore, while performing a process described herein, the computer system 820 can communicate with one or more other computer systems, such as the user 812, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 11 can receive power from a power component 845. The power component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a rechargeable device, etc.

FIG. 12 shows a schematic of an illustrative environment 900 in which the shaving razor cleaning unit 800 depicted in FIG. 11 can be used to facilitate a cleaning treatment of a shaving razor 12 according to an embodiment. In this embodiment, the computer system 820 of the control unit 40 can be configured to control the ultraviolet radiation sources 38 to direct ultraviolet radiation at a surface of the bladed members of the shaving razor 12 as described herein. The sensors 42 are configured to acquire data processed by the computer system 820 to monitor a set of attributes regarding the cleaning treatment of the shaving razor 12 over a period of time. As illustrated, the sensors 42 can acquire data used by the computer system 820 to monitor the set of attributes (e.g., operating parameters, ultraviolet radiation characteristics).

It is understood that the set of attributes for the shaving razor 12 can include any combination of one or more of: a frequency of the usage of the razor 12, a presence of biological activity on a surface of the razor 12, a usage of the razor 12, a disinfection schedule history for the razor 12, and/or the like.

In the case of determining a presence of biological activity on the shaving razor 12, a sensor 42 can also determine a location of the biological activity, a type of biological activity (e.g., type of organism), a concentration of the biological activity, an estimated amount of time an organism has been in a growth phase (e.g., exponential growth and/or stationary), and/or the like. Furthermore, a sensor 42 can determine information on the variation of the biological activity over time, such as a growth rate, a rate with which an area including the biological activity is spreading, and/or the like. In an embodiment, a set of biological activity dynamics are related to various attributes of bacteria and/or virus activity present on a surface of the shaving razor 12, including, for example, the presence of detectable bacteria and/or virus activity, measured bacteria and/or virus population/concentration time dynamics, growth phase, and/or the like.

The computer system 820 can be configured to control and adjust a direction, an intensity, a pattern, and/or a spectral power (e.g., wavelength) of the set of ultraviolet radiation sources 38, based on data received from the sensors 42. The computer system 820 can control and adjust each property of the set of ultraviolet radiation sources 38 independently. For example, the computer system 820 can adjust the intensity, time duration, and/or time scheduling (e.g., including duration (e.g., exposure/illumination time)), duty cycle, time between exposures/illuminations, and/or the like) of the ultraviolet radiation sources 38 for a given wavelength. Each of the properties of the ultraviolet radiation sources 38 can be adjustable and controlled by the computer system 820 according to data provided by the sensors 42.

For example, the computer system 820 can be configured to adjust the direction of the ultraviolet radiation according to a location of the biological activity detected on a surface of the shaving razor 12 using any solution. The computer system 820 can be configured to utilize a target timing, intensity, and/or spectral power of the ultraviolet radiation according to a type of biological activity. That is, the sensors 42 can sense locations of higher levels of biological activity on the surface of the shaving razor 12, and the ultraviolet radiation sources 38 can be configured by the computer system 820 to direct higher doses (by increasing intensity or exposure) of ultraviolet radiation at the locations with higher levels of biological activity (e.g., non-uniform ultraviolet radiation).

In one embodiment, the computer system 820 can be configured to set a periodic or an aperiodic schedule for the ultraviolet radiation when the shaving razor 12 is in place within a housing, receptacle, container or the like. This (periodic or aperiodic) schedule can be interrupted when a sensor senses that a surface of the shaving razor 12 is removed from the housing, receptacle, container or the like. In this manner, the computer system 820 can be configured to turn off the ultraviolet radiation.

As noted above, one of the sensors 42 can include a radiation detector for detecting an amount of radiation to which a surface is exposed during a cleaning treatment. The radiation can include any type of radiation, including, for example, ultraviolet, visible, infrared, microwave, and/or the like. The amount of radiation to which the surface is exposed can be used by the computer system 820 to determine if any additional radiation is required for disinfection.

It is understood that the environment 900 may include the power component 845 to supply power to one or more of the various components depicted in FIG. 12, such as the ultraviolet radiation sources 38, the sensors 42, the computer system 820, and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system, comprising:
a housing to receive a razor blade assembly with at least one bladed member having a top portion and a bottom portion;
at least one ultraviolet radiation source located within the housing to emit ultraviolet radiation towards the top portion and the bottom portion of the bladed member; and
a control unit to initiate a cleaning treatment of the razor blade assembly with the at least one ultraviolet radiation source in response to the razor blade assembly being placed within the housing, the control unit configured for specifying a plurality of operating parameters for the cleaning treatment of the razor blade assembly, the plurality of operating parameters including a cleaning treatment time that the ultraviolet radiation source emits the ultraviolet radiation towards the top portion and the bottom portion of the bladed member, a dosage of ultraviolet radiation delivered by the ultraviolet radiation source, a power setting for operating the ultraviolet radiation source, and a maximum operating temperature.

2. The system according to claim 1, wherein the housing comprises a base member; a pair of opposing grasping members extending outward from a first side of the base member, each grasping member having a first end fixedly attached to the first side of the base member and a second end unattached to the base member, the first end of each grasping member pivotally attached to opposite ends of the first side of the base member, the second end of each grasping member converging towards one another; and a clamping handle attached to a second side of the base member, the clamping handle having a first clamping handle portion and a second clamping portion that both actuate movement of the second ends of the grasping member from a converging position to a diverging open position configured to receive the razor blade assembly, the second ends of the grasping member gripping and covering the razor blade assembly therein in response to the actuating movement being removed from the first clamping handle portion and the second clamping portion.

3. The system according to claim 2, wherein one of the grasping members comprises a plurality of ultraviolet radiation sources configured to emit ultraviolet radiation towards the top portion of the bladed member in response to the gripping and covering of the razor blade assembly, and wherein the other grasping member comprises at least one ultraviolet radiation source configured to emit ultraviolet radiation towards the bottom portion of the bladed member in response to the gripping and covering of the razor blade assembly.

4. The system according to claim 1, wherein an interior surface of the housing comprises an ultraviolet transparent material, the ultraviolet transparent material formed between the ultraviolet radiation source and the razor blade assembly, wherein the ultraviolet transparent material is distinct from the ultraviolet radiation source and the razor blade assembly, and wherein the ultraviolet transparent material comprises one of an ultraviolet transparent fluoropolymer film, an ultraviolet transparent glass and an ultraviolet transparent crystal.

5. The system according to claim 4, wherein the ultraviolet transparent material comprises diffusive elements that diffuse ultraviolet radiation generated from the ultraviolet radiation source to diffusively illuminate the top portion and the bottom portion of the bladed member.

6. The system according to claim 1, wherein an interior surface of the housing comprises a reflective layer to promote recycling of ultraviolet light emitted towards the razor blade assembly.

7. The system according to claim 1, further comprising at least one sensor configured to monitor one of the operating parameters during the cleaning treatment and provide signals thereof to the control unit, wherein the control unit controls operation of the cleaning treatment as a function of the signals received from the sensor.

8. The system according to claim 1, wherein the housing comprises an open-ended container having a cavity formed therein that is configured to receive the razor blade assembly and substantially surround the bladed member upon placement therein.

9. The system according to claim 8, wherein the open-ended container comprises a bifurcated cap having a main body portion, a first bifurcated element and a second bifurcated element opposing the first bifurcated element and separated therefrom, the first bifurcated element and the second bifurcated element each having a first end rigidly fixed to the main body portion and a second end that is flexibly unattached, the main body portion, the first bifurcated element and the second bifurcated element forming an opening that is configured to receive the razor blade assembly.

10. The system according to claim 1, wherein the housing comprises a container having one end with a membrane having a flexible opening insertable into a cavity formed in the container that is configured to receive the razor blade assembly and substantially surround the bladed member upon placement therein.

11. The system according to claim 1, wherein the housing comprises a container having a cavity formed therein, a removable platform suspended in the container that is configured to support the razor blade assembly upon placement therein for irradiation by the ultraviolet radiation source, and a removable cover that fastens to the container and provides access to the cavity and the platform upon removal thereof.

12. The system according to claim 1, wherein the housing comprises an open-ended container having a cavity formed therein and a cleaning fluid reservoir formed in a bottom portion of the cavity that is configured to undergo vibrational movement, wherein the cavity receives the razor blade assembly for substantial immersion within the cleaning fluid reservoir, wherein the ultraviolet radiation source comprises a plurality of ultraviolet radiation sources located about interior surfaces of the cavity and the cleaning fluid reservoir.

13. The system according to claim 1, wherein the housing comprises a container having a cavity formed therein and a cleaning fluid reservoir formed in a bottom portion of the cavity, the container having a surface with an opening into the cavity for insertion of the razor blade assembly, wherein the opening is configured to limit placement of the razor blade assembly cavity to a suspended state held over the cleaning fluid reservoir without immersion therein, wherein the housing comprises a plurality of ultraviolet radiation sources configured to direct ultraviolet radiation to the razor blade assembly, and a cleaning fluid nozzle operating in conjunction with the plurality of ultraviolet radiation sources to direct pressurized cleaning fluid from the cleaning fluid reservoir to the razor blade assembly.

14. A system, comprising:
a housing to receive a razor blade assembly with at least one bladed member having a top portion and a bottom portion;

a plurality of ultraviolet radiation sources located within the housing to emit ultraviolet radiation towards the top portion and the bottom portion of the bladed member, wherein a group of ultraviolet radiation sources irradiates the top portion and at least one ultraviolet radiation source irradiates the bottom portion; and a control unit to initiate a cleaning treatment of the razor blade assembly with the plurality of ultraviolet radiation sources in response to the razor blade assembly being placed within the housing, the control unit configured for specifying a plurality of operating parameters for the cleaning treatment of the razor blade assembly, the plurality of operating parameters including a cleaning treatment time that the ultraviolet radiation sources emit the ultraviolet radiation towards the top portion and the bottom portion of the bladed member, a dosage of ultraviolet radiation delivered by the ultraviolet radiation sources, a power setting for operating the ultraviolet radiation sources, and a maximum operating temperature.

15. The system according to claim 14, wherein the group of ultraviolet radiation sources extend lengthwise over the top portion of the bladed member and the at least one ultraviolet radiation source is centrally located with respect to the bottom portion of the bladed member.

16. The system according to claim 14, wherein a first set of the plurality of ultraviolet radiation sources operate at a first peak wavelength and a second set of the plurality of ultraviolet radiation sources operate at a second peak wavelength, wherein the first peak wavelength is different from the second peak wavelength.

17. The system according to claim 14, wherein a first set of the plurality of ultraviolet radiation sources operate at a target wavelength and intensity designed for disinfection of a first type of bacteria and/or viruses, and a second set of the plurality of ultraviolet radiation sources operate at a different target wavelength and intensity designed for disinfection of a second type of bacteria and/or viruses different from the first type.

18. A system, comprising:
a housing to receive a razor blade assembly with at least one bladed member having a top portion and a bottom portion;
at least one ultraviolet radiation source located within the housing to emit ultraviolet radiation towards the top portion and the bottom portion of the bladed member;
at least one sensor configured to detect conditions within the housing and generate signals representative of the detected conditions, wherein the at least one sensor comprises a bacterial fluorescence sensor that detects a presence of biological activity on the bladed member; and a control unit to initiate a cleaning treatment of the razor blade assembly with the at least one ultraviolet radiation source as a function of the signals generated from the at least one sensor, wherein the control unit receives signals from the bacterial fluorescence sensor and determines whether a cleaning treatment of the razor blade assembly is necessary, wherein the control unit directs the at least one ultraviolet radiation source to initiate a cleaning treatment in response to determining that there is a presence of biological activity on the bladed member that warrants the cleaning treatment, the control unit configured for specifying a plurality of operating parameters for the cleaning treatment of the razor blade assembly, the plurality of operating parameters including a cleaning treatment time that the ultraviolet radiation source emits the ultraviolet radiation towards the top portion and the bottom portion of the bladed member, a dosage of ultraviolet radiation delivered by the ultraviolet radiation source, a power setting for operating the ultraviolet radiation source, and a maximum operating temperature.

19. The system according to claim 18, wherein the at least one sensor is further configured to monitor conditions within the housing during the cleaning treatment of the razor blade assembly and send signals representative of the monitored conditions to the control unit, wherein the bacterial fluorescence sensor is configured to monitor a surface of the bladed member for the presence of biological activity, and the control unit is configured to adjust at least one of an intensity, a wavelength, a pattern, or a duration of the ultraviolet radiation emitted from the at least one ultraviolet radiation source.

20. The system according to claim 18, wherein the control unit is further configured to determine at least one of a location of the biological activity on the bladed member, a type of biological activity present on the bladed member, a concentration of the biological activity, or an estimated amount of time that the biological activity has been in a growth phase, in response to determining that there is a presence of biological activity on the bladed member.

* * * * *